United States Patent
Maar et al.

(10) Patent No.: US 11,066,698 B2
(45) Date of Patent: Jul. 20, 2021

(54) SMALL NUCLEIC ACID QUANTIFICATION USING SPLIT CYCLE AMPLIFICATION

(71) Applicant: Bio-Rad Laboratories, Inc., Hercules, CA (US)

(72) Inventors: Dianna Maar, Mountain House, CA (US); Samantha Cooper, Berkeley, CA (US); Wei Yang, Dublin, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 304 days.

(21) Appl. No.: 15/046,297

(22) Filed: Feb. 17, 2016

(65) Prior Publication Data

US 2016/0265041 A1 Sep. 15, 2016

Related U.S. Application Data

(60) Provisional application No. 62/117,381, filed on Feb. 17, 2015.

(51) Int. Cl.
| | | |
|---|---|---|
| *C12Q 1/6851* | (2018.01) | |
| *C12Q 1/6827* | (2018.01) | |
| *C12Q 1/6848* | (2018.01) | |
| *C12Q 1/6806* | (2018.01) | |
| *C12Q 1/686* | (2018.01) | |

(52) U.S. Cl.
CPC .......... *C12Q 1/6851* (2013.01); *C12Q 1/686* (2013.01); *C12Q 1/6806* (2013.01); *C12Q 1/6827* (2013.01); *C12Q 1/6848* (2013.01)

(58) Field of Classification Search
CPC .......... C12Q 1/6851; C12Q 2525/161; C12Q 2525/204; C12Q 2527/107; C12Q 1/6827; C12Q 2531/113; C12Q 1/6806; C12Q 1/686
USPC ...................................................... 435/91.2
See application file for complete search history.

(56) References Cited

U.S. PATENT DOCUMENTS

| | | |
|---|---|---|
| 2002/0142331 A1 | 10/2002 | Fu et al. |
| 2009/0123912 A1 | 5/2009 | Raymond |
| 2009/0142745 A1* | 6/2009 | Breidenthal .......... B01F 3/1271 435/3 |
| 2010/0047784 A1 | 2/2010 | Shlomit et al. |
| 2010/0120097 A1 | 5/2010 | Matz et al. |
| 2010/0304978 A1 | 12/2010 | Deng |
| 2011/0294676 A1 | 12/2011 | Cawthon |
| 2014/0004569 A1* | 1/2014 | Lambowitz ........ C12N 15/1096 435/91.21 |
| 2014/0113332 A1 | 4/2014 | Betts et al. |
| 2014/0221238 A1 | 8/2014 | Regan et al. |
| 2014/0274786 A1 | 9/2014 | McCoy et al. |
| 2014/0295434 A1 | 10/2014 | Wu et al. |
| 2016/0177376 A1 | 6/2016 | Tan et al. |

FOREIGN PATENT DOCUMENTS

| | | |
|---|---|---|
| CN | 102676637 A | 9/2012 |
| CN | 103205489 A | 7/2013 |
| WO | 2011/158784 A1 | 12/2011 |
| WO | 2013/113748 A1 | 8/2013 |
| WO | 2017/117287 A1 | 7/2017 |

OTHER PUBLICATIONS

Liu, et al., "Robust dosage-PCR for detection of heterozygous chromosomal deletions", Biotechniques, vol. 34, No. 3, Mar. 2003, pp. 558-570.
Cantrell, et al., "X Chromosome Inactivation and Xist Evolution in a Rodent Lacking LINE-1 Activity", PLos One, vol. 4, Jul. 2009, pp. 1-9.
Ishii, et al., "Optimization of Annealing Temperature To Reduce Bias Caused by a Primer Mismatch in Multitemplate PCR", Appl Environ Microbiol., vol. 67, No. 8, Aug. 2001, pp. 3753-3755.
PCT/US2016/018328, "International Search Report and Written Opinion", dated Jul. 29, 2016, 18 pages.
Extended European Search Report in EP Application 18212633.4 dated Feb. 13, 2019; 82 pages.
Hale, M. et al.; "Next-generation pyrosequencing of gonad transcriptomes in the polyploid lake sturgeon (*Acipenser fulvescens*): the relative merits of normalization and rarefaction in gene discovery"; *BMC Genomics*; BioMed Central; vol. 10, No. 1; Apr. 29, 2009; 11 pages.
Zhu, Y.Y.; "Reverse Transcriptase Template Switching: A SMART™ Approach for Full-Length cDNA Library Construction"; *BioTechniques*; vol. 30; Apr. 2001; pp. 892-897.
Partial European Search Report in EP Application 16753003.9 dated Jul. 2, 2018; 19 pages.
Hindson, C. et al.; "Absolute quantification by droplet digital PCR versus analog real-time PCR"; *Nature Methods*; vol. 10, No. 10; Sep. 1, 2013; pp. 1003-1005.

* cited by examiner

*Primary Examiner* — Cynthia B Wilder
(74) *Attorney, Agent, or Firm* — Kilpatrick Townsend and Stockton LLP

(57) ABSTRACT

Methods of detecting or quantifying short RNA or DNA molecules using split cycle amplification are provided.

21 Claims, 15 Drawing Sheets

Specification includes a Sequence Listing.

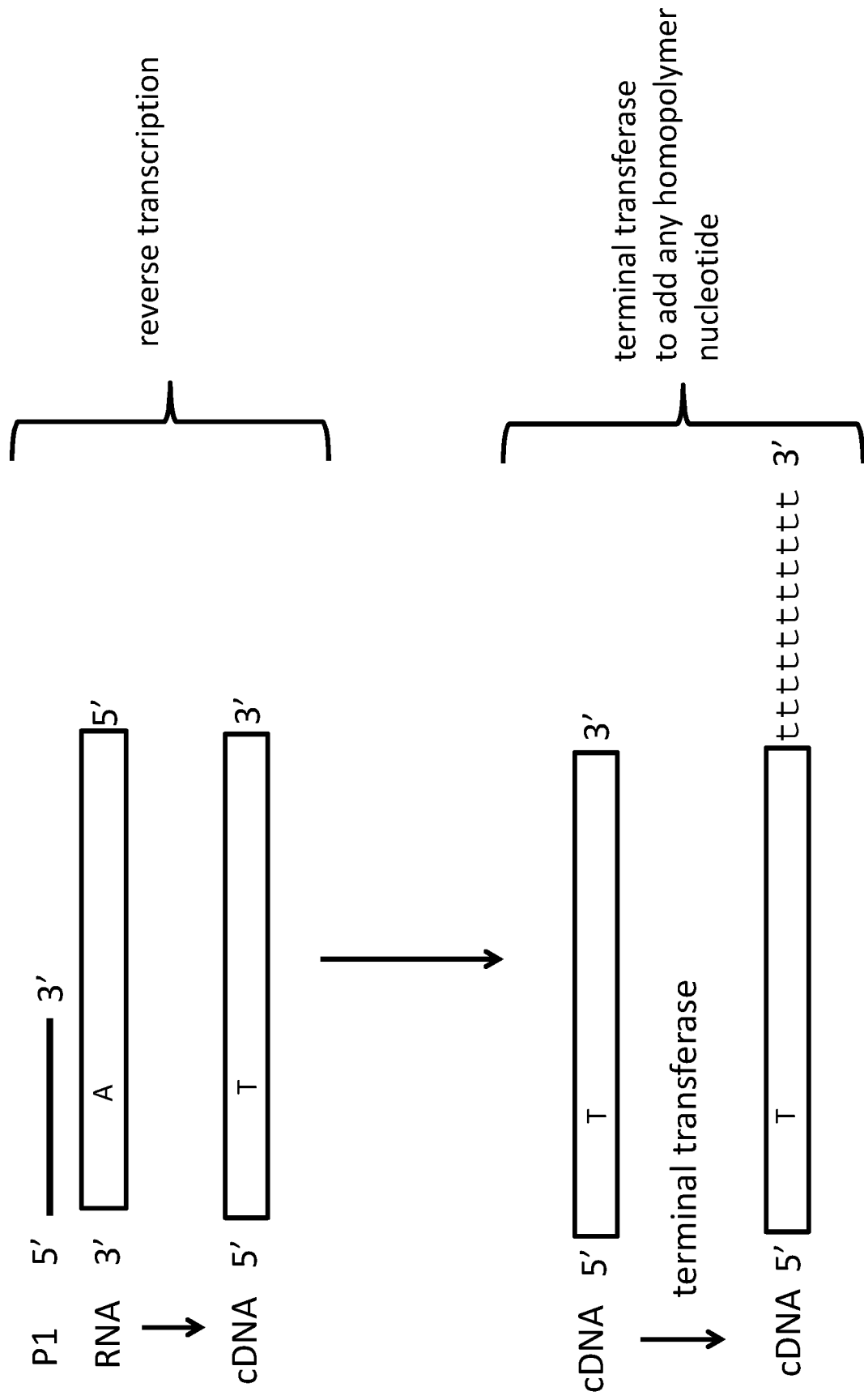

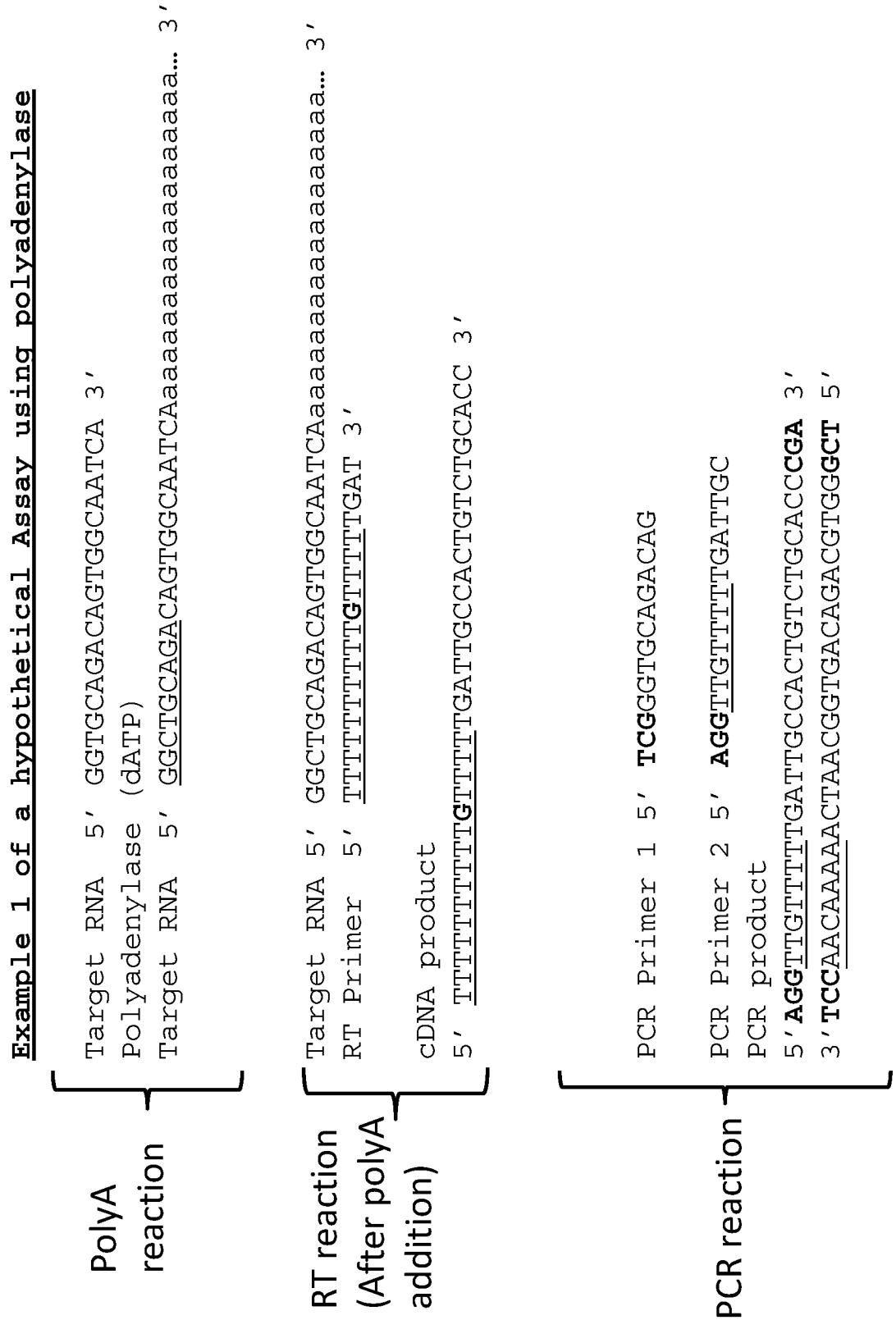

FIGURE 8
Example 3 of a hypothetical Assay using terminal transferase

RT reaction:
```
Target RNA    5' GGTGCAGACAGTGGCAATCA 3'
RT Primer     5' TGATTGCCAC 3'
cDNA product
              5' TGATTGCCACTGTCTGCACC 3'
```

Terminal Transferase Reaction:
```
              5' TGATTGCCACTGTCTGCAGTA 3'
Terminal Transferase (dTTP)
...tttttttttttttttttttTGATTGCCACTGTCTGCACC
```

PCR reaction:
```
PCR Primer 1  5' TCGGGGTGCAGACAG
PCR Primer 2  5' AGGTTTTTTTTTTGATTGC PCR product
5' AGGTTTTTTTTTTGATTGCCACTGTCTGCACCCGA 3'
3' TCCAAAAAAAAAACTAACGGTGACAGACGTGGGCT 5'
```

SMALL NUCLEIC ACID QUANTIFICATION USING SPLIT CYCLE AMPLIFICATION

CROSS-REFERENCES TO RELATED APPLICATIONS

This application claims priority to U.S. Provisional Application No. 62/117,381, filed Feb. 17, 2015, the contents of which are hereby incorporated by reference in the entirety for all purposes.

BACKGROUND OF THE INVENTION

A number of types of non-coding short RNAs occur in cells. Examples of such RNAs include but are not limited to miRNA, snoRNA, piRNA, or lncRNA. Other types of RNA include, for example, mRNA. Shorter RNAs in particular can present difficulties for amplification because of the sequences do not present a long enough sequence to hybridize and amplify using standard primers and methods.

Conventional PCR amplification and detection of nucleic acid targets that are shorter than 30 nucleotides long can be difficult. PCR amplification requires that the primers used for amplification anneal to the target DNA or RNA at a temperature that is within the range of the polymerase used in the reaction. Since PCR requires the reaction to be heated to 90° C. or higher during each cycle in order to melt the duplexes of nucleic acid materials, the polymerase must be heat stable. This is achieved by utilizing polymerases from thermophiles and results in an enzyme that functions best at temperatures centering on 60° C. but can range between 40° C. and 75° C. As temperatures get near the lower and higher ranges of the range of temperature the polymerase is less efficient resulting in an ideal primer melting temperature between 50° C. and 65° C. This requirement results in primers that are between about 15 and 30 nucleotides in length. Therefore the minimum amplicon or target length is about 30-60 nucleotides for DNA binding dye detection and 45-90 nucleotides for Taqman probe-based detection. These lengths also depend on the GC content of the target so that, for example, a very AT-rich target would require a much longer amplicon length than a GC-rich one.

BRIEF SUMMARY OF THE INVENTION

In some aspects, methods of quantitating an amount of a target DNA template in a sample are provided. In some embodiments, the method comprises:
a) forming a plurality of mixture partitions, wherein the mixture partitions comprise:
  i) the target DNA template;
  ii) a thermostable DNA dependent DNA polymerase; and
  iii) a forward and a reverse amplification primer, wherein the amplification primers comprise a 3' hybridization region that hybridizes to the target DNA template and primes template directed extension of the primer in the presence of the DNA dependent DNA polymerase;
the forward or the reverse amplification primer optionally further comprises a 5' tail region that is not complementary to the target DNA template; and
the forward and reverse amplification primers optionally have a combined length greater than the length of the target DNA template; and
b) incubating the mixture partitions under thermal cycling conditions suitable for amplification of the target DNA template by a polymerase chain reaction, wherein the thermal cycling conditions comprise a first set of temperature cycles and a second set of temperature cycles, wherein the second set of temperature cycles comprises an annealing temperature that is at least 5° C. higher than an annealing temperature of the first set of temperature cycles; and
c) detecting the presence or absence of amplified target DNA template in the mixture partitions and determining the fraction of partitions where the target DNA template is present; thereby quantifying the amount of target DNA template in the sample.

In some embodiments, the 5' tail region of the forward or the reverse amplification primers or both have at least 15%, 20%, 25%, 30%, 35%, 40%, 45%, or 50% GC content. In some embodiments, the 5' tail region of the forward or the reverse amplification primers or both have between 15% and 80%, 15% and 75%, 15% and 70%, 15% and 65%, 15% and 60%, 15% and 50%, 15% and 45%, 15% and 40%, 20% and 80%, 20% and 75%, 20% and 70%, 20% and 65%, 20% and 60%, 20% and 50%, 20% and 45%, 20% and 40%, 30% and 80%, 30% and 75%, 30% and 70%, 30% and 65%, 30% and 60%, 30% and 50%, or 30% and 45% GC content.

In some embodiments, the target DNA template in the partitions is at an average concentration of 0.001-10 copies per partition.

In some embodiments, the first cycling condition comprises 1-15, 2-15, 5-15, 10-15, 1-20, 2-20, 5-20, 10-20, 15-20, 1-10, 2-10, or 5-10 cycles.

In some embodiments, the thermal cycling conditions further comprise a third set of temperature cycles comprising an annealing temperature that is at least 5° C. higher (e.g., at least 10°, 15°, or 20°, e.g., 5-25°, 5-20° C.) than the annealing temperature of the second set of temperature cycles.

In some embodiments, the first cycling condition comprises 1-20 cycles (e.g., 1-15, 2-15, 5-15, 10-15, 2-20, 5-20, 10-20, 15-20, 1-10, 2-10, or 5-10 cycles) of:
i) a denaturation step;
ii) a combined primer annealing and extension step; and
iii) optionally, a second annealing and extension step at a higher temperature than in the first primer annealing and extension step.

In some embodiments, the second cycling condition comprises 10-50 cycles (e.g., 10, 20, 30, 40, or 50 cycles). In some embodiments, the second cycling condition comprises 10-50 cycles (e.g., 10, 20, 30, 40, or 50 cycles) of: i) a combined primer annealing and extension step; and ii) a denaturation step.

In some embodiments, the first cycling condition comprises an annealing temperature of less than 55° C. or 50° C. (e.g., from 50° C. to 40° C., or from 55° C. to 40° C.).

In some embodiments, the second cycling condition comprises an annealing temperature of at least 60° C., 55° C. or 50° C. (e.g., from 50° C. to 60° C., 50° C. to 65° C., 50° C. to 68° C., 55° C. to 60° C., 55° C. to 65° C., or 55° C. to 68° C.).

In some embodiments, the amplification primers hybridize to opposite strands of the target DNA template and flank a region of the target DNA template having an annealing temperature of less than 55° C. or 50° C.

In some embodiments, the amplification primers hybridize to opposite strands of the target DNA template and flank a region of the target DNA template between 1-30 (e.g., 1-10, 8-12, 8-20, 10-25) nucleotides in length.

In some embodiments, the amplification primers hybridize to opposite strands of the target DNA template such that 3' ends of the primers hybridize to adjacent nucleotide positions in the target DNA template, i.e. zero intervening nucleotides.

In some embodiments, the amplification primers hybridize to opposite strands of the target DNA template and the 3' ends of the amplification primers overlap when hybridized to the target DNA template. In some embodiments, the length of the overlap is 1, 2, or 3 nucleotides.

In some embodiments, the 3' hybridization regions of the amplification primers are at least 3, 4, 5, 6, 7, 8, 9, 10, 11, 12, 13, 14, 15, 16, 17, 18, 19, 20, or more nucleotides in length.

In some embodiments, the 3' hybridization regions of the amplification primers are less than 10, 11, 12, 13, 14, 15, 16, 17, 18, 19, 20, 21, 22, 23, 24, 25, 26, 27, 28, 29, or 30 nucleotides in length.

In some embodiments, the target DNA template is less than 100, 95, 90, 85, 80, 75, 70, 65, 60, 55, 50, 45, 40, or 35 nucleotides in length. In some embodiments, the target DNA template is between 100 and 15, 100 and 25, 100 and 35, 90 and 15, 90 and 25, or 90 and 35, nucleotides in length. In some embodiments, the target DNA template comprises a region complementary to an RNA (e.g., microRNA), wherein the region complementary to the RNA or microRNA is less than 50, 35, 30, 25, 22, 20, 18, or 15 nucleotides in length. In some embodiments, the target DNA template comprises a region complementary to an RNA (e.g., microRNA), wherein the region complementary to the RNA or microRNA is between 50 and 15, 50 and 18, 50 and 20, 50 and 22, 50 and 25, 50 and 30, 50 and 35, 35 and 15, 35 and 18, 35 and 20, 35 and 22, 35 and 25, or 35 and 30 nucleotides in length.

In some embodiments, the 5' tail region is at least 1, 2, 3, 4, 5, 6, 7, 8, 9, 10, 11, 12, 13, 14, 15, 16, 17, 18, 19, or 20 nucleotides in length. In some embodiments, the 5' tail region is between 1 and 20, 2 and 20, 3 and 20, 4 and 20, 5 and 20, 1 and 15, 2 and 15, 3 and 15, 4 and 15, 5 and 15, 1 and 10, 2 and 10, 3 and 10, 4 and 10, or 5 and 10 nucleotides in length.

In some embodiments, incubating comprises conditions such that the 3' hybridization region of the forward or the reverse amplification primer does not hybridize to and prime template directed extension from a second DNA template having a polymorphism in the region to which the amplification primer is hybridized. In some embodiments, the 3' hybridization region of the forward or the reverse amplification primer comprises a discriminatory nucleotide, wherein the discriminatory nucleotide is complementary to the target DNA template but is not complementary to the second DNA template having the polymorphism, and wherein the discriminatory nucleotide is at the ultimate position from the 3' end of the primer or is 1, 2, 3, 4, or 5 nucleotides from the 3' end. In some embodiments, the 3' hybridization region of the forward or the reverse amplification primer comprises a discriminatory nucleotide, wherein the discriminatory nucleotide is complementary to the target DNA template but is not complementary to the second DNA template having the polymorphism, and wherein the discriminatory nucleotide is at a position at least 1, 2, 3, 4, 5, 6 or more nucleotides from the 3' end of the primer and wherein the 3' hybridization region of the forward or the reverse amplification primer further comprises a nucleotide that is not complementary to the target DNA template or the second DNA template.

In some embodiments, the 3' hybridization region of the forward or reverse amplification primer comprises a homopolymeric region of at least 1, 2, 3, 4, or 5 nucleotides that is complementary to a homopolymeric region of the target DNA template. In some embodiments, the homopolymeric region of the primer is between 3 and 25 contiguous nucleotides in length. In some embodiments, the homopolymeric region is 3' of a 5' tail region that is not complementary to the target DNA template. In some embodiments, the homopolymeric region of the primer is a polythymine region. In some embodiments, the homopolymeric region of the primer is a polyadenine region. In some embodiments, the method comprises adding a homopolymeric region to the target DNA template by contacting the target DNA template with a terminal transferase enzyme. In some embodiments, the homopolymeric region of the target DNA template is a polythymine region.

In some embodiments, the forming of the plurality of mixture partitions comprising the target DNA template comprises reverse transcribing a target RNA template to form the target DNA template. In some embodiments, reverse transcribing the target RNA template comprises hybridizing a reverse transcription primer to the target RNA template, wherein the target RNA template is polyadenylated at the 3' end, and the reverse transcription primer comprises from 3' to 5':

i) a 3' hybridization region that hybrids to the target RNA template nucleic acid; and one of:

ii) a homopolymeric region that is complementary to a region of the polyadenylated 3' end of the target RNA template; or iii) a region that is homopolymeric except has one or two nucleotides that are different from remaining nucleotides in the region, wherein the region, except for said one or two nucleotides (which are bounded on either side by homopolymeric sequence), is complementary to a region of the polyadenylated 3' end of the target RNA template.

In some embodiments, the homopolymeric region is a polythymine region. In some embodiments, the homopolymeric region is a polyadenine region. In some embodiments, the homopolymeric region is a polycytosine region. In some embodiments, the homopolymeric region is a polyguanine region. In some embodiments, the homopolymeric region is from 2 to 15 nucleotides in length. In some embodiments, reverse transcribing the target RNA template comprises hybridizing a reverse transcription primer to the target RNA template and generating a cDNA, wherein the target RNA template is polyadenylated at the 3' end and the cDNA has a complementary polyT sequence at the 5' end of the cDNA, and the method further comprises adding a homopolymeric region to the 3' end of the cDNA, thereby generating a cDNA having homopolymeric sequences at 5' and 3' ends.

Also separately provided is a method of generating and amplifying cDNA. This method can optionally also be combined with the methods described above or elsewhere herein. In some embodiments, the method comprises a. reverse transcribing a target RNA comprising a non-polyA region and a polyA tail by:

i. hybridizing a reverse transcription (RT) primer to the target RNA, wherein the RT primer comprises from 5' to 3':

$$X-(T)_m-Y-(T)_n-Z$$ (SEQ ID NO: 1)

wherein X is an optional (i.e., may be absent) 5' tail nucleotide sequence of 1-10 (e.g., 1-5 or 2-5) nucleotides that is not complementary to the target RNA;

T is thymine;

Y is a single nucleotide that is C, G, or A;

Z is an optional sequence of 1-10 (e.g., 1-5, 2-5, or 2-10) nucleotides that is complementary to a portion of the non-polyA region adjacent to the polyA tail;

m is 1-20 (e.g., 1-10 or 2-10);
n is 1-20 (e.g., 1-10 or 2-10);
ii. reverse transcribing the target RNA by extending the RT primer with a RNA-dependent polymerase to generate a cDNA incorporating the RT primer; and
b. amplifying the cDNA by:
i. hybridizing an amplification primer comprising a sequence complementary to the $-(T)_m-Y-(T)_n-Z$; and
ii. extending the amplification primer with a DNA-dependent polymerase.

In some embodiments, m=1-4 or 2-4, n=1-4 or 2-4, or both m and n are independently 1-4 or 2-4. In some embodiments, the RT primer comprises Z (1-10 (e.g., 1-5, 2-5, or 2-10) nucleotides that are complementary to a portion of the non-polyA region adjacent to the polyA tail) and the amplification primer comprises one or more 3' nucleotides adjacent to sequence complementary to the $-(T)_m-Y-(T)_n$ that are complementary to Z.

In some embodiments, the amplifying comprises a polymerase chain reaction (e.g., including but not limited to a digital PCR reaction).

BRIEF DESCRIPTION OF THE DRAWINGS

As shown in FIGS. 1A and 1B, a first set of cycles of amplification are performed as a lower annealing and extension temperature followed by a second set of cycles at a higher annealing and extension temperature.

FIG. 3A shows the reverse transcription step with primer P1 that includes a 3' region (A) that is complementary to the RNA (SEQ ID NO:16), a homopolymeric polyT region that is complementary to the polyA sequence of the RNA, and may or may not include a non-homopolymeric nucleotide somewhere within the homopolymeric region of the primer (B). Reverse transcription results in the bottom molecule in FIG. 3A. In many embodiments, the RT primer does not include the nucleotide being discriminated.

FIG. 3B illustrates the first set of amplification cycles using the cDNA as a target DNA, with primers P1 and P2 being used to amplify the target with the complementary region (A) of the primers annealing during this set of amplification. FIG. 3C illustrates the second set of amplification cycles with higher temperature annealing and extension temperatures with both region A and B of the primers will anneal and amplify.

FIGS. 4A, 4B, and 4C schematically illustrate additional aspects in which a homopolymeric sequence is added to the initial cDNA 3' end (e.g., by terminal transferase). In the embodiment shown, polyT is added to the cDNA in FIG. 4A (SEQ ID NO:18 (poly-T)), though other nucleotide homopolymers (e.g., polyA, polyU, polyG, polyC) can be added. FIG. 4B illustrates the first set of amplification cycles using the cDNA as a target DNA, with primers P1 and P2 being used to amplify the target, with P2 including a homopolymeric segment that is complementary to the homopolymer on the cDNA sequence (SEQ ID NO:18 (poly-T) and SEQ ID NO:19 (poly-A)). FIG. 4C illustrates the second set of amplification cycles with higher temperature annealing and extension temperatures.

FIG. 5B illustrates the first set of amplification cycles using the cDNA as a target DNA, with primers P1 and P2 being used to amplify the target, with P1 including a homopolymeric segment that is complementary to the homopolymer on the cDNA sequence. FIG. 5C illustrates the second set of amplification cycles with higher temperature annealing and extension temperatures (SEQ ID NO:18 (poly-T) and SEQ ID NO:19 (poly-A)).

FIG. 6 illustrates hypothetical use of polyadenylase to a target RNA. SEQ ID NOs are as follows: PolyA reaction: Target RNA (top)=SEQ ID NO:20, Target RNA (bottom)=SEQ ID NO:21; RT reaction: Target RNA=SEQ ID NO:21, RT primer=SEQ ID NO:22, cDNA product=SEQ ID NO:23; PCR reaction: primers (SEQ ID NOS:24-25), PCR products (SEQ ID NO:26-27).

FIG. 8 illustrates a hypothetical example involving introduction of a homopolymeric sequence using terminal transferase. SEQ ID NOs are as follows: RT reaction: Target RNA=SEQ ID NO:21, RT primer=SEQ ID NO:28, cDNA product=SEQ ID NO:29; Terminal Transferase Reaction: top sequence=SEQ ID NO:30, Terminal Transferase=SEQ ID NO:31, PCR reaction: primers (SEQ ID NOS:24 and 33), PCR products (SEQ ID NO:34-35).

DEFINITIONS

Figure 1A:
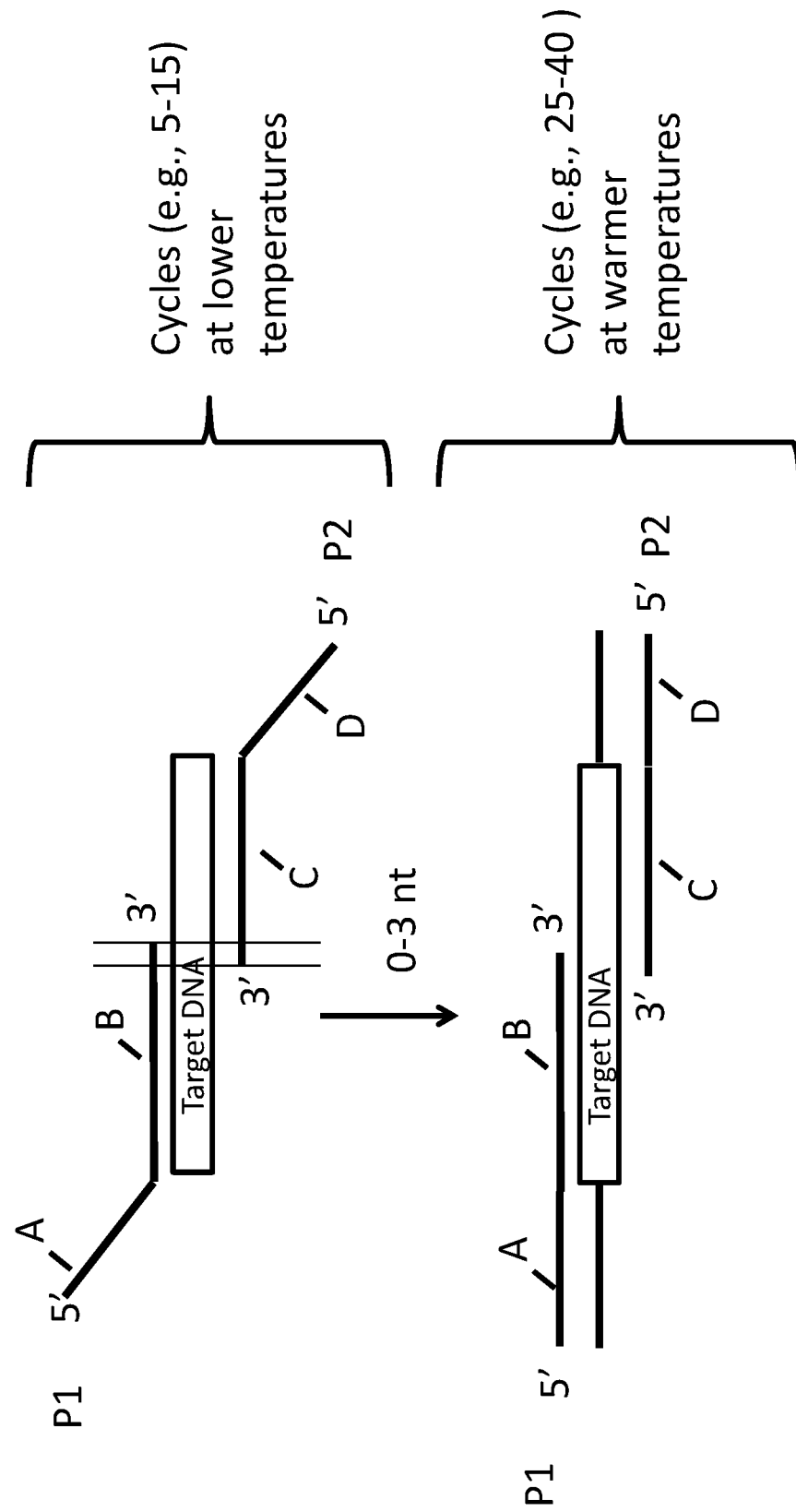
FIG. 1A illustrates a schematic example of primers P1 and P2 used to amplify a target DNA. P1 has a 5' tail region (A) that is not complementary to the target DNA and a 3' region (B) that is complementary to the target DNA. P2 has a 5' tail region not complementary to the target DNA and a 3' region complementary to the opposite strand of the target DNA (SEQ ID NOs:13-14). The target DNA is shown as a block. It will be appreciated that the target DNA can start as a single-stranded or double-stranded nucleic acid but that upon amplification, the amplicon will be double stranded.

The term "polymerase" refers to an enzyme that performs template-directed synthesis of polynucleotides. The term encompasses both a full length polypeptide and a domain that has polymerase activity. DNA polymerases are well-known to those skilled in the art, and include but are not limited to DNA polymerases isolated or derived from *Pyrococcus furiosus, Thermococcus litoralis*, and *Thermotoga maritime*, or modified versions thereof. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In $E.$ $coli$, three types of DNA polymerases have been found, DNA polymerases I (family A), II (family B), and III (family C). In eukaryotic cells, three different family B polymerases, DNA polymerases $\alpha$, $\delta$, and $\epsilon$, are implicated in nuclear replication, and a family A polymerase, polymerase $\gamma$, is used for mitochondrial DNA replication. Other types of DNA polymerases include phage polymerases. Similarly, RNA polymerases typically include eukaryotic RNA polymerases I, II, and III, and bacterial RNA polymerases as well as phage and viral polymerases. RNA polymerases can be DNA-dependent and RNA-dependent. The polymerases described herein can be heterologous to the target nucleic acid(s) in a reaction mixture, mixture partition, or set of mixture partitions. As used herein, the term "heterologous" refers to two components (e.g., target nucleic acid and polymerase) that are not found together in nature, e.g., because they are not found together in the same wild-type organism.

"Thermally stable polymerase," as used herein, refers to any enzyme that catalyzes polynucleotide synthesis by addition of nucleotide units to a nucleotide chain using DNA or RNA as a template and has an optimal activity at a temperature above 45° C.

The term "nucleic acid amplification" or "amplification reaction" refers to any in vitro means for multiplying the copies of a target sequence of nucleic acid. Such methods include but are not limited to polymerase chain reaction (PCR), DNA ligase chain reaction (see U.S. Pat. Nos. 4,683,195 and 4,683,202; PCR Protocols: A Guide to Methods and Applications (Innis et al., eds, 1990)), (LCR), QBeta RNA replicase, and RNA transcription-based (such as TAS and 3SR) amplification reactions as well as others known to those of skill in the art.

"Amplifying" refers to a step of submitting a solution to conditions sufficient to allow for amplification of a polynucleotide. Components of an amplification reaction include, e.g., primers, a polynucleotide template, polymerase, nucleotides, and the like. The term amplifying typically refers to an "exponential" increase in target nucleic acid. However, amplifying as used herein can also refer to linear increases in the numbers of a select target sequence of nucleic acid, such as is obtained with cycle sequencing.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step. PCR can be performed as end-point PCR (i.e., only monitored at an end point) or as quantitative PCR (monitored in "real time").

An "olignucleotide primer" or "primer" refers to an oligonucleotide sequence that anneals to a sequence on a target nucleic acid and serves as a point of initiation of nucleic acid synthesis.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide nucleic acids (PNAs).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, $\gamma$-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "partitioning" or "partitioned" refers to separating a sample into a plurality of portions, or "partitions." Partitions can be solid or fluid. In some embodiments, a partition is a solid partition, e.g., a microchannel. In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

DETAILED DESCRIPTION OF THE INVENTION

I. Introduction

Methods and reaction mixtures have been discovered for the amplification of RNA targets, and particularly, short RNA targets such as, but not limited to, micro RNAs. The RNA target is initially reverse transcribed into a target DNA. In other embodiments, the methods and reaction mixtures can be used to amplify a target DNA (e.g., a DNA other than cDNA). The methods involve using a first and a second set of amplification cycles (e.g., PCR cycles) to amplify the target DNA, in which the second set of cycles comprise an annealing temperature at a higher temperature than the annealing temperature of the first set of conditions. In addition, forward and reverse amplification primers are provided wherein the primers both have a 3' region complementary to the target DNA and at least one (or both) of the primers have a 5' tail that is not complementary to the target. The first set of cycles is performed at an annealing temperature to allow for amplification based on hybridization of the 3' regions of the primers to the target DNA. Following a number of cycles (e.g., 5-10 or 5-15) in the first set, an amplicon is established that incorporates the 5' tail(s) of the primers, thereby forming a longer amplicon to which the tailed primer(s) hybridize with a higher Tm, allowing for the second set of cycles to have a higher annealing and extension temperature at which the polymerase functions better (closer or at optimal).

Also provided is a method of reverse transcribing a polyadenylated (polyA) RNA into a cDNA and amplifying the cDNA using a reverse transcription primer that comprises a polyT sequence containing one or two intervening nucleotides that are nucleotides other than T, thereby generating a cDNA having a modified polyT sequence comprising the one or two intervening nucleotides. The cDNA can then be amplified using a primer complementary to the modified polyT sequence. The inventors have found this method results in higher specificity and sensitivity than using an otherwise identical primer but lacking the intervening nucleotides.

Exemplary target RNAs that can be detected and amplified using the methods described herein include, but are not limited to, miRNA, snRNA, snoRNA, piRNA, or lncRNA.

MicroRNAs (miRNAs), typically 18 to 25 nt in length, are non-protein-coding RNAs that can inhibit the translation of target mRNAs (see, e.g., Croce and Calin, Cell 122(1): 6-7 (2005)). Other small RNAs include small nucleoplasmic RNAs (snRNAs) and small nucleolar RNAs (snoRNAs). These small RNA molecules can function, for example, in mRNA splicing (U1, U2, and U4 to U6 snRNAs), mRNA and rRNA processing (U7 snRNA; U3 and U8 snoRNAs), and site selection for RNA modification by methylation of the 2' hydroxyl group (box C/D snoRNAs) or by pseudouridine formation (box H/ACA snoRNAs). Piwi-interacting RNAs (piRNAs) were identified through association with Piwi proteins in mammalian. piRNAs can range from 26-30 nucleotides in length. Long noncoding RNA (lncRNA) have also been described.

Additional aspects of the inventions are provided herein.

II. Reaction Components

Reaction components can include a sample comprising target DNA and a forward primer and reverse primer as described herein.

The methods described herein can be performed as one or more polymerase chain reaction (PCR) amplification. The methods are particularly useful in partitioned PCR methods such as digital PCR. Thus in some embodiments, a plurality of reaction mixtures are prepared each having a low average copy number of target DNA. For example, in some embodiments, the average target DNA copy number is 0.001-10 copies per partition (e.g., 0.01, 0.05, 0.1, 0.5, 1, 2, 3, 4, 5, 6, 7, 8, 9, or 10 copies per partition). The number of partitions can vary as understood in the art but can range, for example, from 1000-$10^{10}$ partitions or more.

The reaction mixture will comprise at least two oligonucleotide primers, referred here only to differentiate them as "forward" and "reverse" primers. Each primer will have a 3' region that hybridizes to the target DNA. The 3' region of the primers can be, for example, 3-20 nucleotides long, (e.g., 3, 4, 5, 6, 7, 8, 9, 10, 11, 12, 13, 14, 15 or more, e.g., 5-15, 8-12, 5-20, etc.). In some embodiments, the 3' regions are fully complementary to the corresponding target DNA sequence. In other embodiments, the 3' region can have at most one or two mismatches with the target DNA sequence. As discussed above and elsewhere herein, the methods involve employing at least two different sets of cycles of amplification with the second set of cycles having a warmer annealing temperature than the first set. The 3' regions of the primers can be selected to have a melting temperature (Tm) close to, for example, at or below the second annealing temperature. For example, in some embodiments, the Tm of one or both 3' regions is approximately the same as or within 5, 10, 15, 20, 25, or 30 (e.g., 3-20, 3-25) degrees C. lower than the annealing temperature of the second set of cycles.

Figure 1B:
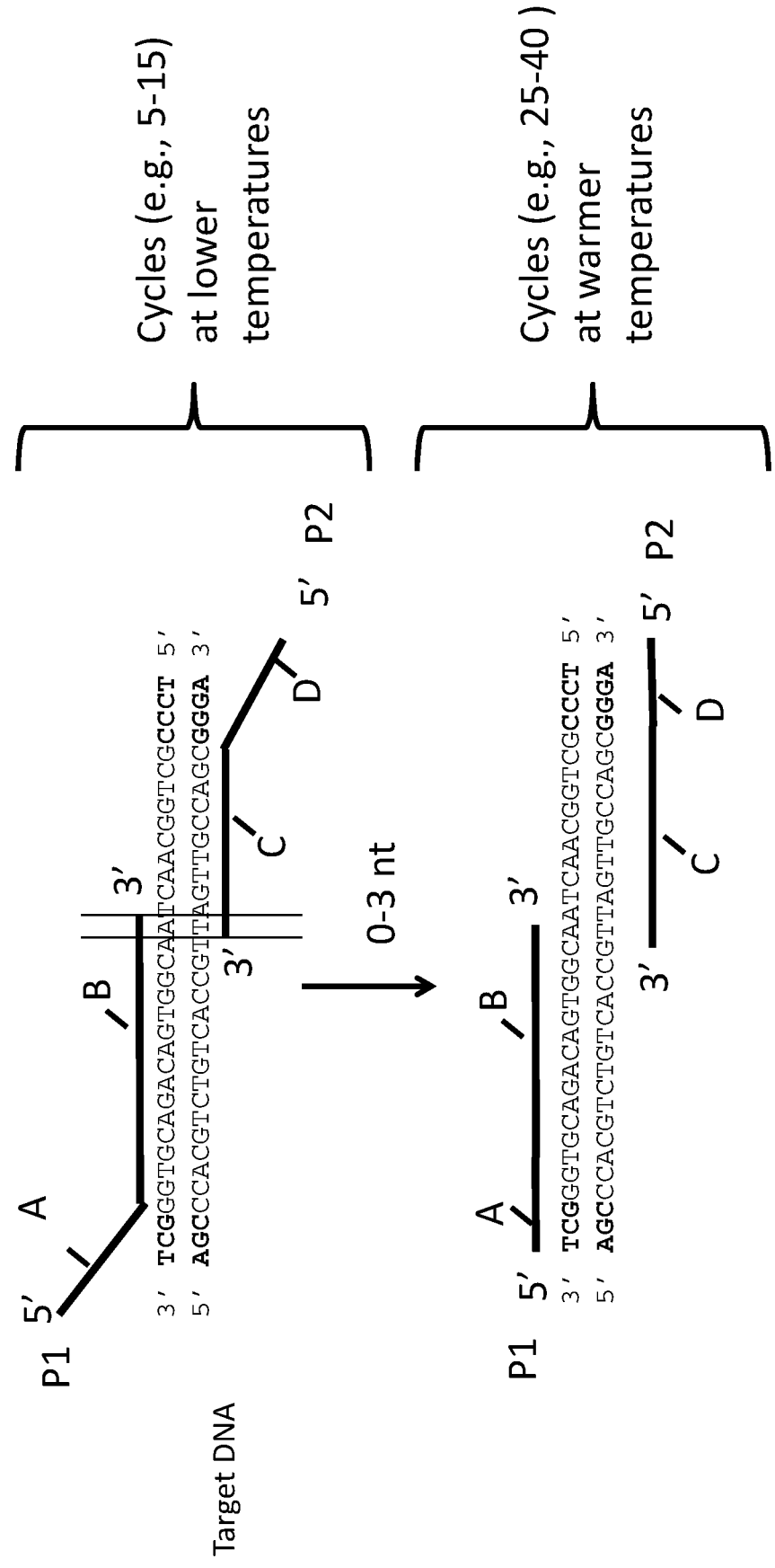

FIGS. 1A-B show an example of some of the different components of the mixture. Primers P1 and P2 are shown. Primer regions B and C are the 3' regions of the primers P1 and P2, respectively. It will be appreciated that primer P1 hybridizes to one strand of the target DNA and primer P2 hybridizes to the opposing strand of the target DNA. In cases where the initial target DNA is single-stranded, the amplicon after the first cycle will include a second strand.

The forward primer, reverse primer, or both, can also have a 5' tail region that does not hybridize to the target DNA. This 5' tail region can function to lengthen the amplicon in rounds of amplification after the initial amplification rounds. For example, initial rounds of amplification will result in an amplicon comprising the target DNA sequence as well as the 5' tail region. The top section of FIG. 1 illustrates one embodiment in which the 3' regions of the primers hybridize to the target DNA while the 5' regions do not. Sequence of the 5' tail region can be selected so that the Tm of the primer as a whole (3' region and 5' region) has a Tm at or below the extension temperature of the second set of amplification cycles. In some embodiments, the Tm of the primer as a whole is approximately the same as or within 5, 10, 15, 20, 25, or 30 degrees C. lower than the annealing temperature of the second set of cycles. The sequences of the forward and reverse primers will generally be selected to avoid primer dimer formation or for self-hybridization of primers. In some embodiments, the 5' regions are selected to have a GC content of greater than 30, 40, 50, 60, 70, 80, 85, 90, or 95%, e.g., 100%. The length of the 5' tail region can vary as desired. For example, in some embodiments, the 5' tail region ii 1-20 nucleotides long, e.g., 1, 2, 3, 4, 5, 7, 10 nucleotides, etc.). In some embodiments, the 5' tail portion (not counting the remaining of the primer) has a Tm at or lower than the first annealing temperature.

Figure 2:
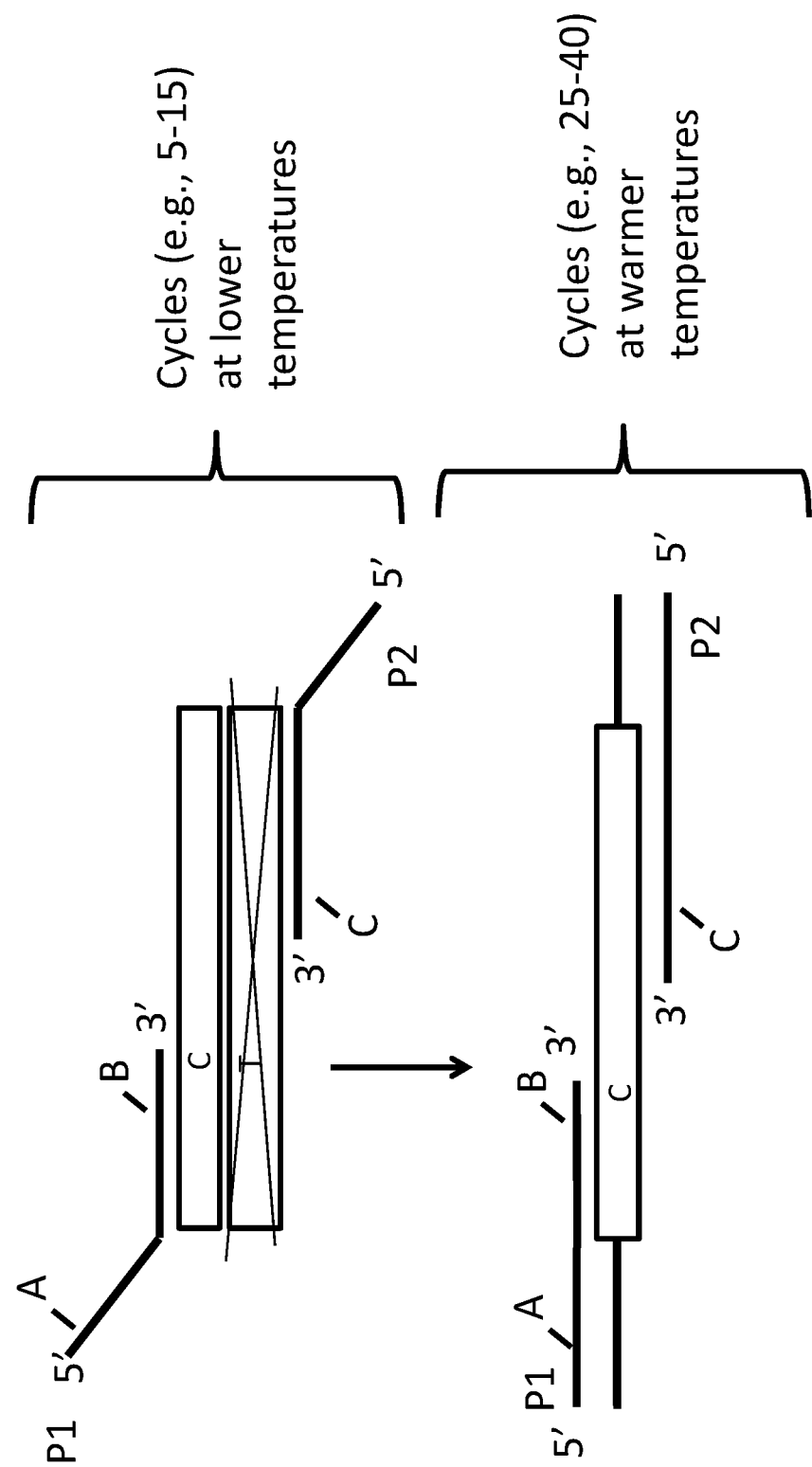
FIG. 2 illustrates a schematic example in which the amplifications are performed on a sample having a target DNA and a non-target DNA that differs from the target DNA by one nucleotide (shown as the target DNA having a "C" and the non-target DNA having a "T"). As in FIG. 1, the target DNA is shown as a box and could be single- or double stranded, with the resulting amplicon being double-stranded. The "X" through the non-target DNA indicates that sequence is not amplified because the 3' region of primer P1 is complementary to the target DNA and the conditions used for amplification do not allow for significant amplification of the non-target DNA.

In some embodiments, a target DNA will be highly similar to a non-target DNA sequence. For example, where the target DNA is a cDNA from a microRNA to be detected but a non-target microRNA is highly similar, a contaminating cDNA from the non-target microRNA can interfere with detection. To reduce false positives, in some embodiments, the 3' region of one or both primers is selected so that the 3' region is not fully complementary (e.g. at least one or two nucleotides are not complementary) to the non-target DNA. In some embodiments, the non-complementary nucleotide(s) (relative to the non-target DNA), also referred to herein as "discriminatory nucleotides," is located at the 3' end of the primer or is 1, 2, 3, 4, or 5 nucleotides from the 3' end. Because a DNA target can be very short, in some embodiments, the non-complementary nucleotide can be positioned farther than 5 nucleotides from the 3' end of the primer. This aspect is depicted in FIG. 2 where two DNA sequences, one containing the target C and the other DNA sequence comprising a T at the same position. Primer P1 comprises a 3' region completely complementary to the target DNA (i.e., has a G to complement the target C), but has a non-complementary nucleotide with regard to the non-target DNA. Annealing and extension conditions can then be selected such that the primer hybridizes to the target but does not hybridize to the non-target. "Does not hybridize" in this context means that the target DNA is amplified at least 10 times, and in some embodiments, at least 100 or 1000 times the amount the non-target DNA is amplified.

In some cases, it can be helpful to further select a nucleotide in another location in the 3' region of the primer to mis-match with both the target and non-target DNA. This will reduce the Tm of the primer for the target but the Tm for the non-target DNA will be even lower because the 3' region will be mismatched at two locations. By setting the annealing temperature below the Tm for the target and above the Tm for the non-target DNA, the target can be amplified with little or no non-target DNA amplified.

Positioning of the area of hybridization of the forward and reverse primers on the target DNA will be a function, in part, of the 3' region of the primers. Thus, the 3' region of the forward primer will have a binding site on the target DNA and the 3' region of the reverse primer will have a binding site on the target DNA (on opposing strands of a double stranded target DNA). In some embodiments, two binding sites will have one or more nucleotides (e.g., 1-25, 1-10, 8-12 nucleotides) between the binding sites in the target DNA. In other embodiments, the binding sites will be adjacent (no nucleotides between the two binding sites is shown in FIG. 1A-B where the gap is "0"). In yet another embodiment, the binding sites of the two primers will be overlapping. For example, the binding sites can overlap by 1, 2, 3, 4 or more (e.g., 1-3) nucleotides. This aspect is depicted in FIG. 1 where the overlap is indicated a being "0-3," meaning that in some embodiments, the binding sites overlap by 3 nucleotides, in other embodiments the binding sites overlap by 2 nucleotide, in other embodiments the binding sites overlap by 1 nucleotide or are adjacent ("0" gap).

In some embodiments, the target DNA will further comprise a homopolymeric sequence on the 5' end, 3' end, or both. Homopolymeric sequences are sequences of at least 2, 3, 4, 5, 6, 7, 8, 9, 10, or more (e.g., 3-10, 3-20, 3-50) adjacent identical nucleotides. Exemplary homopolymeric sequences include polyA, polyT, polyG, polyC, or polyU sequences. In embodiments in which the target DNA has one or more homopolymeric sequence the corresponding primer for amplification of the target can have a complementary homopolymeric sequence. Exemplary aspects are illustrated, for example in FIGS. 3A-C, 4A-C and 5A-C. The homopolymeric sequence in the primers need not be the same length as the homopolymeric sequence in the target DNA. For example, the primer homopolymeric sequence can be shorter than the target homopolymeric sequence. In some embodiments, one or both primers will have homopolymeric sequences complementary to homopolymeric sequences in the target DNA and one or more of the primers will further comprise a 5' tail region that is not complementary to the target DNA.

Target DNA can be generated from any biological sample. An advantage of the present methods is the ability to amplify short sequences and thus in some embodiments, the target DNA is less than 90, 80, 70, 60, 50, 40, 35 or 30 nucleotides, for example, between 10-30, 20-30, 20-40, 20-50, or 10-90 nucleotides in length. In many embodiments, the DNA is a cDNA from an RNA present in a sample. The sample can be for example, any mixture containing a short RNA. In many embodiments, the sample is derived from a biological fluid, cell or tissue. The sample can be crude or purified. In some cases, the sample is a preparation of RNA from a cell or cells. In some embodiments, the cells are animal cells, including but not limited to, human, or non-human, mammalian cells. Non-human mammalian cells include but are not limited to, primate cells, mouse cells, rat cells, porcine cells, and bovine cells. In some embodiments, the cells are plant or fungal (including but not limited to yeast) cells. Cells can be, for example, cultured primary cells, immortalized culture cells or can be from a biopsy or tissue sample, optionally cultured and stimulated to divide before assayed. Cultured cells can be in suspension or adherent prior to and/or during the permeabilization and/or DNA modification steps. Cells can be from animal tissues, biopsies, etc. For example, the cells can be from a tumor biopsy.

In some embodiments, samples include RNA or DNA targets that only have short amplifiable regions (e.g., wherein a target region has less than 50, 40, 30, 25, or 20 contiguous amplifiable nucleotides), degraded, or are otherwise difficult to amplify due to nucleic acid degradation. For example, formalin-fixed samples can have only short sequences of nucleic acid due to fixation. In other embodiments, ancient nucleic acid samples or samples that have been exposed to chemical or temperature conditions that degrade nucleic acids can be amplified by the methods described herein in view of the method's ability to amplify shorter sequences than typically can be amplified in PCR.

In other embodiments, the same basic components of the reaction mixture as described above can be used to amplify any cDNA or other DNA molecule, whether longer or shorter. These aspects are of particular interest when distinguishing a target DNA from a different non-target DNA that differs by a single nucleotide. In these aspects, the 3' region of one primer (e.g., one which also has a 5' tail sequence as described above) is relatively short (e.g., 3-18, 5-19, 8-22, 3-8, 5-10 nucleotides) with one of the nucleotides in the 3' region being complementary to the nucleotide in the target DNA that differs in the non-target DNA. By selecting a shorter 3' region, the difference in Tm for the target DNA compared to the non-target DNA will be accentuated, thus allowing for a relatively short complementary region to distinguish between target and non-target DNA. Additionally this method is not prone to the DNA polymerase's misreading or error rates during extension for the discrimination since this method uses a non-hybridized 3' nucleotide to prevent the extension step from beginning on non-target templates. After a first set of cycles at this lower Tm for the target DNA, the resulting amplicon will incorporate the 5' tail sequence(s) and thus a second set of amplification cycles at a higher Tm can be used as described elsewhere herein. Because this aspect can be used for longer target sequences, the primers can be designed to accommodate a labeled probe (e.g., a Taqman or molecular beacon probe) if desired. In other embodiments, an intercalating dye as described elsewhere herein can be used to detect the amplification product.

III. Methods

The methods described herein provide for amplification with at least two different sets of amplification cycles where the second set of amplification cycles has an annealing temperature higher than the first set of cycles. In some embodiments, the second set of amplification cycles has an annealing temperature at least 1, 2, 3, 4, 5, 6, 7, 8, 9, or 10 (e.g., 5-15) degrees C. higher than the first set of amplification cycles. In some embodiments, the first set of cycles employ an annealing temperature of less than, e.g., 55, 50, 48, or 45° C. In some embodiments, the second set of cycles employ an annealing temperature of more than, e.g., 50, 55, or 60° C. (e.g., 50-75° C.).

In some embodiments, the number of cycles in the first set of cycles will be smaller than the number of cycles in the second set. In part, this can be because the first set of cycles generates the initial amplicon comprising the incorporated primers, after which the second set of cycles can then continue to amplify the enlarged amplicon with greater efficiency. In some embodiments, the first set of cycles will have between 3-20 cycles, e.g., 5-15 cycles. In some embodiments, the second set of cycles will have at least 15 cycles, e.g., between 15-45, 15-40, 20-40, 25-35 cycles.

An amplification "cycle" refers to a series of temperature changes that support denaturation of double stranded DNA, annealing of primers to the target DNA, and extension of the primers by a DNA polymerase. Typically, a three-step or two-step cycle is used. A three-step cycle comprises a separate denaturation step (e.g., 90-98 degrees C.), a separate annealing step (e.g., 50-65 degrees C.), and a separate extension step (e.g., 65-75 degrees C.). In a two-step cycle, a denaturation step as described above is followed by a combined annealing/extension step (e.g., 50-65 degrees C.). While this document refers to the second set of cycles having a higher annealing temperature than the first set, it should be understood that in a two-step cycle, the extension step of the second set of cycles will also necessarily be higher than in the first set of cycles. In a three-step cycle, the extension step can be but does not necessarily have to be higher in the second set of cycles compared to the extension step in the first set of cycles.

As noted above, one use of the described methods is for detection and quantifying small RNAs including but not limited to miRNA, snoRNA, piRNA, or lncRNA. As such, prior to the steps described above, a reverse transcription reaction can be performed to generate a cDNA. Reverse transcription can be performed as desired using a reverse transcriptase to generate a cDNA. Any of a variety of reverse transcriptases can be used. Exemplary reverse transcriptases include but are not limited to murine leukemia virus (MLV) reverse transcriptase, Avian Myeloblastosis Virus (AMV) reverse transcriptase, Respiratory Syncytial Virus (RSV) reverse transcriptase, Equine Infectious Anemia Virus (EIAV) reverse transcriptase, Rous-associated Virus-2 (RAV2) reverse transcriptase, SUPERSCRIPT II reverse transcriptase, SUPERSCRIPT I reverse transcriptase, THERMOSCRIPT reverse transcriptase and MMLV RNase H⁻ reverse transcriptases. In additional embodiments, a DNA polymerase that functions as an RNA polymerase can be used. For example, Tth and Z05, which are DNA polymerases, can function as reverse transcriptase in the presence of manganese. The concentration of the reverse transcriptase can vary and optimal concentrations can be determined empirically and depend on the particular reverse transcriptase used.

In some embodiments, the RNA from the sample of interest contains a polyA tail. However, many small RNAs do not necessarily have a polyA tail. In some embodiments, a polyA tail can be added to an RNA prior to generation of the cDNA. For example, the RNA can be incubated with poly(A) polymerase and ATP to polyadenylate the RNA. This step can then be followed by reverse transcription as described herein.

Once a target DNA is available, one can add a homopolymeric 3' sequence, for example by ligation or incubating the DNA with terminal transferase and a single nucleotide (e.g., dTTP, dATP, dGTP, dCTP, dUTP). The resulting DNA molecule will comprise the original target DNA sequence and a 3' homopolymer. In some embodiments, a homopolymeric sequence will be added to both ends of the target DNA using one or more of the methods described herein (e.g., polyadenylation of the RNA and a polyT sequence can be added to the DNA with terminal transferase). In embodiments where a homopolymeric sequence has been added to the RNA, the resulting template for amplification will be longer, making design of primers for amplification easier and allowing for higher temperature for annealing in amplification. Also poly adenylation or other methods of lengthening the cDNA can allow for the discrimination of the target by providing enough sequence to place the 3' end of the PCR primer over the nucleotide(s) to be discriminated within 1, 2, 3, 4 or 5 nucleotides of a primer's 3' end.

Also provided is a method of reverse transcribing an RNA having a polyA tail. This method can be performed separate from the above described split-cycle method (e.g., for any reverse transcription purpose) or can be used in conjunction with the split-cycle method described herein. In some embodiments, the RNA will naturally comprise a polyA tail (for example, mRNA). In other aspects the polyA tail can be added to an RNA using poly A polymerization. See, e.g., Cao, G. J. and Sarkar, N. Proc. Natl. Acad. Sci. USA. 89, 10380-10384 (1992).

Once a polyA-containing RNA is provided, the RNA can be reverse transcribed using a reverse transcription (RT) primer wherein the RT primer comprises from 5' to 3':

$$X-(T)_m-Y-(T)_n-Z \quad \text{(SEQ ID NO: 1)}$$

wherein X is an optional 5' tail nucleotide sequence of 1-10 nucleotides that is not complementary to the target RNA;
T is Thymine;
Y is a single nucleotide that is C, G, or A;
Z is an optional sequence of 1-10 nucleotides that is complementary to a portion of the non-polyA region adjacent to the polyA tail;
m is 1-10 (e.g., 2-10, 2-5); and
n is 1-10 (e.g., 2-10, 2-5).

The above-described primer does not have a single homopolymeric polyT sequence complementary to the polyA sequence of the RNA and instead has a polyT sequence divided by (having polyT on both side of) one or two nucleotides other than T. Thus, when the RT primer hybridizes to the polyA RNA, the polyT portions of the RT primer will hybridize to the polyA portion of the RNA, but the one or two nucleotides other than T will not be complementary to the polyA portion and will form a "bulge" and area of non-hybridization. Because RT conditions are selected to allow for hybridization nevertheless, the primer will prime the RT reaction to generate a cDNA. Notably, the resulting cDNA will contain at its 5' end a complementary sequence to the one or two nucleotides. This will allow for much more specific amplification of the cDNA in subsequent amplification that uses a primer complementary to the $-(T)_m-Y-(T)_n$ sequence. As an Example, if the RT primer was 5'tttttCtttttacgc (i.e., m=5, Y=C, n=5; (SEQ ID NO:2)), 3' a PCR primer could be: 5'gcgtaaaaagaaaaa 3' (SEQ ID NO:3).

In some embodiments, the RT primer will include one or more 3' nucleotides that specifically hybridize to the 3' end of the non-polyA portion of the target RNA, thereby making the RT primer more specific. For instance, in the above example, "acgc" is a sequence complementary to the last four non-polyA nucleotides of a target RNA (and accordingly the PCR primer has a complementary "gcgt" sequence).

The amplification reactions described herein can be detected as desired. In some embodiments, a label that generates signal in the presence of double-stranded DNA is used. In some embodiments, intercalating agents that produce a signal when intercalated in double stranded DNA may be used. Exemplary agents include SYBR GREEN™, SYBR GOLD™, and EVAGREEN™. Since these agents are not template-specific, it is assumed that the signal is generated based on template-specific amplification. This can be confirmed, if desired, by monitoring signal as a function of temperature because melting point of template sequences will generally be much higher than, for example, primer-dimers, etc.

Detection and quantification of target DNAs is preferably carried out by digital PCR. In general aspects, digital PCR is carried out by partitioning a dilute sample into a plurality of discrete partitions such that most of the plurality of discrete test sites comprise on average a low number of initial target DNA copies. Amplification products are then analyzed and quantified, resulting in a representation of the presence or absence of genomic regions of interest corresponding to the presence or absence of the target DNA. The number of target DNA (and thus target RNA) copies can then be quantified to estimate the number of target DNA copies in a sample. The number of partitions may vary depending on the application and the level of statistical confidence to be achieved.

The separated sample comprising target DNA (or RNA if reverse transcription is to occur in the partitions) can be partitioned into a plurality of partitions. Partitions can include any of a number of types of partitions, including solid partitions (e.g., wells or tubes) and fluid partitions (e.g., aqueous droplets within an oil phase). In some embodiments, the partitions are droplets. In some embodiments, the partitions are microchannels. Methods and compositions for partitioning a sample are described, for example, in published patent applications WO 2010/036352, US 2010/0173394, US 2011/0092373, US2014/0170736, and US 2011/0092376, the entire content of each of which is incorporated by reference herein.

In some embodiments, the sample is partitioned into a plurality of droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes.

In some embodiments, the droplet is formed by flowing an oil phase through an aqueous solution comprising the label(s) to be detected. In some embodiments, the aqueous sample comprising the label(s) to be detected comprises a buffered solution and reagents for detecting the label(s). The oil for the oil phase may be synthetic or naturally occurring. In some embodiments, the oil comprises carbon and/or silicon. In some embodiments, the oil comprises hydrogen and/or fluorine. Exemplary oils include, but are not limited to, silicone oil, mineral oil, fluorocarbon oil, vegetable oil, or a combination thereof.

The oil phase may comprise a fluorinated base oil which may additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH may be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H, 2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules may behave as bioreactors able to retain their contents through an incubation period. The conversion to microcapsule form may occur upon heating. For example, such conversion may occur at a temperature of greater than about 40°, 50°, 60°, 70°, 80°, 90°, or 95° C. During the heating process, a fluid or mineral oil overlay may be used to prevent evaporation. Excess continuous phase oil may or may not be removed prior to heating. The biocompatible capsules may be resistant to coalescence and/or flocculation across a wide range of thermal and mechanical processing.

In some embodiments, the sample is partitioned into at least 500 partitions (e.g., droplets), at least 1000 partitions, at least 2000 partitions, at least 3000 partitions, at least 4000 partitions, at least 5000 partitions, at least 6000 partitions, at least 7000 partitions, at least 8000 partitions, at least 10,000 partitions, at least 15,000 partitions, at least 20,000 partitions, at least 30,000 partitions, at least 40,000 partitions, at least 50,000 partitions, at least 60,000 partitions, at least 70,000 partitions, at least 80,000 partitions, at least 90,000 partitions, at least 100,000 partitions, at least 200,000 partitions, at least 300,000 partitions, at least 400,000 partitions, at least 500,000 partitions, at least 600,000 partitions, at least 700,000 partitions, at least 800,000 partitions, at least 900,000 partitions, at least 1,000,000 partitions, at least 2,000,000 partitions, at least 3,000,000 partitions, at least 4,000,000 partitions, at least 5,000,000 partitions, at least 10,000,000 partitions, at least 20,000,000 partitions, at least 30,000,000 partitions, at least 40,000,000 partitions, at least 50,000,000 partitions, at least 60,000,000 partitions, at least 70,000,000 partitions, at least 80,000,000 partitions, at least 90,000,000 partitions, at least 100,000,000 partitions, at least 150,000,000 partitions, or at least 200,000,000 partitions.

In some embodiments, the sample is partitioned into a sufficient number of partitions such that at least a majority of partitions have no more than 1, 2, 3, 4, 5, 6, 7, 8, 9, 10, 15, 20, 30, 40, 50, 60, 70, 80, 90, 100, 200, 300, 400, or 500 copies of a label. In some embodiments, a majority of the partitions have no more than 1, 2, 3, 4, 5, 6, 7, 8, 9, 10, 15, 20, 30, 40, 50, 60, 70, 80, 90, 100, 200, 300, 400, or 500 copies of the one or more labels to be detected. In some embodiments, on average no more than 1, 2, 3, 4, 5, 6, 7, 8, 9, 10, 15, 20, 30, 40, 50, 60, 70, 80, 90, 100, 200, 300, 400, or 500 copies of the one or more labels are present per partition.

In some embodiments, the sample is partitioned into a sufficient number of partitions such that, on average, at least one partition lacks a copy of the label. In some embodiments, the sample is partitioned into a sufficient number of partitions such that, on average, at least 5, 10, 15, 20, 25, 30, 35, 40, 50, 60, 70, 80, 90, 100, 125, 150, 175, 200, 250, 300, 350, 400, 450, or 500 partitions lack a copy of the label. In some embodiments, the sample is partitioned into a sufficient number of partitions such that, on average, at least 5, 10, 15, 20, 25, 30, 35, 40, 50, 60, 70, 80, 90, 100, 125, 150, 175, 200, 250, 300, 350, 400, 450, or 500 partitions lack a copy of the label and such that, on average, at least 5, 10, 15, 20, 25, 30, 35, 40, 50, 60, 70, 80, 90, 100, 125, 150, 175, 200, 250, 300, 350, 400, 450, or 500 partitions have at least one copy of the label.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, in some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

A digital readout assay, e.g., digital analysis, can be used to detect and quantify RNA or DNA in a sample by partitioning the sample and reaction components and then amplifying the reactions with the primers and as described herein with at least two sets of amplification cycles. Generally, the process of digital analysis involves determining for each partition of a sample whether the partition is positive or negative for the presence of the label or labels to be detected. For quantification the partitions are examined for the presence or absence of a detectable signal in each partition. A partition is "positive" for the presence of the antigen if a signal is detected in the partition. A partition is "negative" if no signal detected in the partition.

In some embodiments, a detector that is capable of detecting a signal or multiple signals is used to analyze each partition for the presence or absence of signal. For example, in some embodiments a two-color reader (fluorescence detector) is used. The fraction of positive-counted partitions can enable the determination of absolute concentrations for the target DNA or RNA to be measured.

Once a binary "yes-no" result has been determined for each of the partitions of the sample, the data for the partitions is analyzed using an algorithm based on Poisson statistics to quantify the amount of target in the sample. Statistical methods for quantifying the concentration or amount of target are described, for example, in WO 2010/036352, which is incorporated by reference herein in its entirety.

DNA polymerases useful in the present invention can be any polymerase capable of replicating a DNA molecule. Exemplary DNA polymerases are thermostable polymerases, which are especially useful in PCR. Thermostable polymerases are isolated from a wide variety of thermophilic bacteria, such as *Thermus aquaticus* (Taq), *Thermus brockianus* (Tbr), *Thermus flavus* (Tfl), *Thermus ruber* (Tru), *Thermus thermophilus* (Tth), *Thermococcus litoralis* (Tli) and other species of the *Thermococcus* genus, *Thermoplasma acidophilum* (Tac), *Thermotoga neapolitana* (The), *Thermotoga maritima* (Tma), and other species of the *Thermotoga* genus, *Pyrococcus furiosus* (Pfu), *Pyrococcus woesei* (Pwo) and other species of the *Pyrococcus* genus, *Bacillus sterothermophilus* (Bst), *Sulfolobus acidocaldarius* (Sac) *Sulfolobus solfataricus* (Sso), *Pyrodictium occultum* (Poc), *Pyrodictium ahyssi* (Pah), and *Methanohacterium thermoautotrophicum* (Mth), and mutants, variants or derivatives thereof.

In some embodiments, the polymerase enzyme is a hybrid polymerase comprising a polymerase domain and a DNA binding domain. Such hybrid polymerases are known to show an increased processivity. See e.g., U.S. Patent Application Publication Nos. 2006/005174; 2004/0219558; 2004/0214194; 2004/0191825; 2004/0081963; 2004/0002076; 2003/0162173; 2003/0148330; 2003/0138830 and U.S. Pat. Nos. 6,627,424 and 7,445,898, each of which is hereby incorporated by reference in its entirety for all purposes and in particular for all teachings related to polymerases, hybrid/chimeric polymerases, as well as all methods for making and using such polymerases. In one aspect, the hybrid polymerases lack 3'-5' exonuclease activity. In one embodiment, such hybrid polymerases comprise a double point mutation in the polymerase domain that provides this exonuclease deficiency. In a specific embodiment, hybrid polymerases can comprise the double point mutation D141A/E143A in the polymerase domain.

In some embodiments, the binding domain of hybrid polymerases is from a thermostable organism and provides enhanced primer annealing at higher temperatures, e.g., temperatures above 45° C. For example, Sso7d and Sac7d are small (about 7 kd MW), basic chromosomal proteins from the hyperthermophilic archaeabacteria *Sulfolobus solfataricus* and *S. acidocaldarius*, respectively (see, e.g., Choli et al., *Biochimica et Biophysica Acta* 950:193-203, 1988; Baumann et al., *Structural Biol.* 1:808-819, 1994; and Gao et al, *Nature Struc. Biol.* 5:782-786, 1998). These proteins bind DNA in a sequence-independent manner and when bound, increase the Tm of DNA by up to 40° C. under some conditions (McAfee et al., *Biochemistry* 34:10063-10077, 1995). These proteins and their homologs are often used as the sequence-non-specific DNA binding domain in improved polymerase fusion proteins. Sso7d, Sac7d, Sac7e and related sequences (referred to herein as "Sso7 sequences" or "Sso7 domains") are known in the art (see, e.g., accession numbers (P39476 (Sso7d); P13123 (Sac7d); and P13125 (Sac7e)). These sequences typically have at least 75% or greater, of 80%, 85%, 90%, or 95% or greater, amino acid sequence identity. For example, an Sso7 protein typically has at least 75% identity to an Sso7d sequence.

In further embodiments, hybrid polymerases of use are described for example in U.S. Patent Application Publication Nos. 2006/005174; 2004/0219558; 2004/0214194; 2004/0191825; 2004/0081963; 2004/0002076; 2003/0162173; 2003/0148330; 2003/0138830; PCT Publication No. WO 2012/138417; and U.S. Pat. Nos. 6,627,424 and 7,445,898, each of which is hereby incorporated by reference in its entirety for all purposes and in particular for all teachings related to polymerases, hybrid/chimeric polymerases, as well as all methods for making and using such polymerases. Examples of hybrid polymerase proteins and methods of generating hybrid proteins are also disclosed in WO2004011605, which is hereby incorporated by reference in its entirety for all purposes, and in particular for all teachings related to generating hybrid proteins.

Many of the steps (e.g., reverse transcription, amplification, etc.) described above can be performed using routine conditions used in the field of recombinant genetics. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999).

Example

Figure 7:
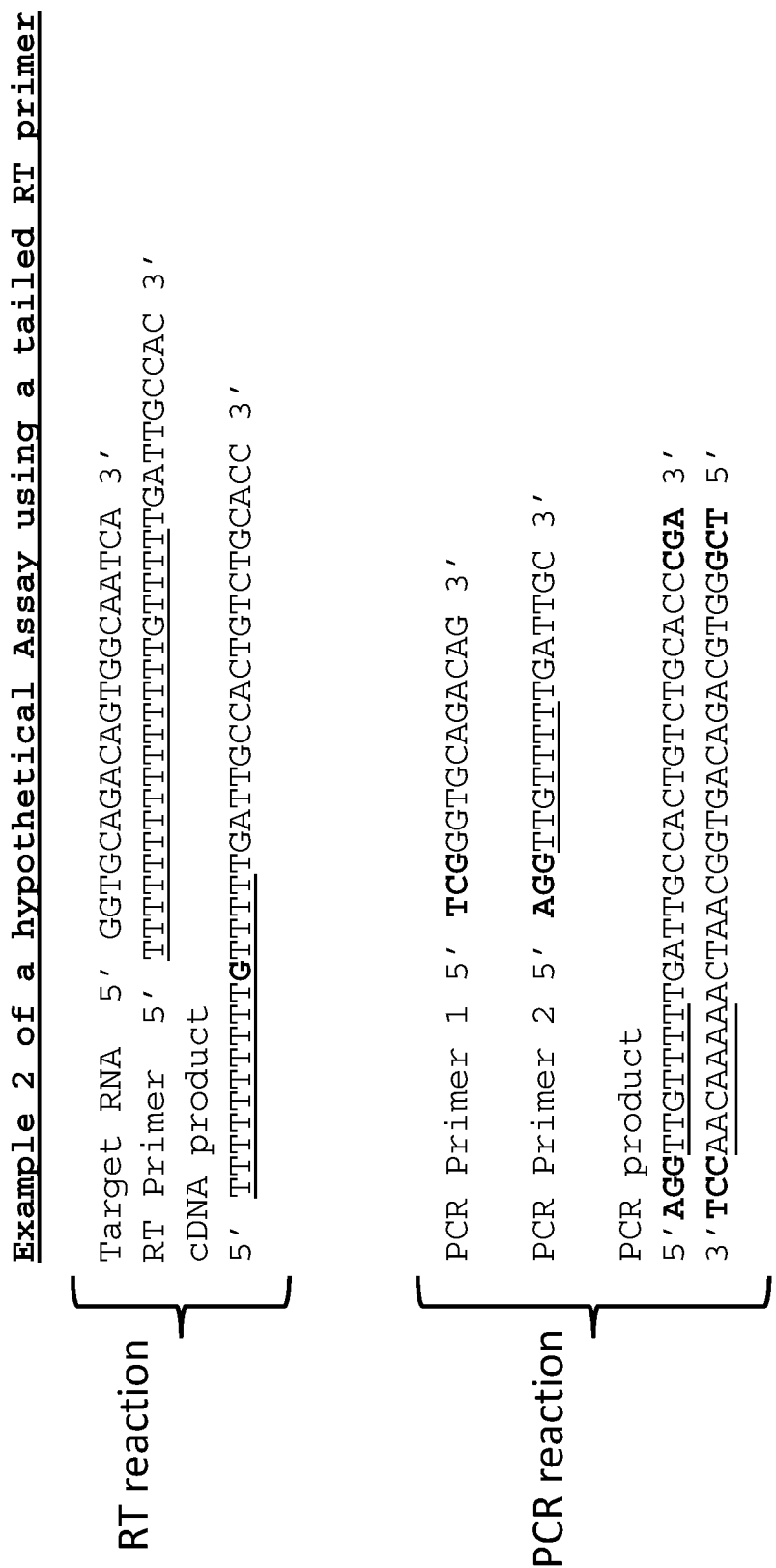
FIG. 7 illustrates a second hypothetical example in which a tailed primer is used. SEQ ID NOs are as follows: RT reaction: Target RNA=SEQ ID NO:20, RT primer=SEQ ID NO:32, cDNA product=SEQ ID NO:23; PCR reaction: primers (SEQ ID NOS:24-25), PCR products (SEQ ID NO:26-27).

FIGS. 6-8 provide example schemes for various aspects. FIG. 6 illustrates hypothetical use of polyadenylase to a target RNA ("PolyA reaction"). The poly adenylated RNA is subsequently reverse transcribed with an RT primer. The RT primer includes a non-T nucleotide (in this example a G) in the middle of the homopolymeric polyT sequence that complements the added polyA sequence on the RNA, thereby producing a cDNA with a 5' polyT sequence comprising the non-T nucleotide. A PCR reaction is subsequently performed (optionally a split cycle as described herein) using a primer comprising a portion of the polyT sequence and having the intervening non-T nucleotide (for example, the PCR primer 2 underlined sequence). Both PCR primers uses include a 5' tail sequence shown in bold.

FIG. 7 illustrates a second hypothetical example in which a tailed primer is used. The RT reaction section of the figure shows a RT primer comprising a 3' section complementary to the target RNA and an underlined 5' tail that is not complementary to the target RNA. Following reverse transcription the shown "cDNA product" is produced. The cDNA product is then amplified in a PCR reaction (e.g., a split cycle amplification as described herein) using Primer 1, which has a bolded 5' non-complementary tail and a 3' section (normal font) complementary to the cDNA product, and Primer 2, which comprises a 5' non-complementary tail, a middle segment (underlined) that contains at least a portion of the 5' tail of the cDNA as introduced by the RT primer 5' tail, and a 3' region that is complementary to the resulting double-stranded cDNA.

FIG. 8 illustrates a hypothetical example involving introduction of a homopolymeric sequence using terminal transferase. In the RT reaction, the target RNA is reverse transcribed with a specific selective RT primer that is complementary to the target RNA. While a 5' tail is not used in this example, one could use such a tail. Subsequently, the cDNA is used in a terminal transferase to add a homopolymeric sequence (as shown, polyT) to the 5' end of the cDNA. The cDNA product is then amplified in a PCR reaction (e.g., a split cycle amplification as described herein) using Primer 1 having a bolded 5' non-complementary tail and a 3' region complementary to the cRNA (normal font) and Primer 2 in-frame with the cDNA strand and comprising a 5' non-complementary tail section, an underlined sequence comprising at least a portion of the homopolymeric sequence, and a 3' region.

In a working example, Synthetic DNA (22 nucleotides plus homopolymer sequence of 15 Adenosine nucleotides) and primers containing tailed 5' regions as described (Integrated DNA Technologies, Coralville, Iowa) were added to EvaGreen ddPCR Supermix Cat #186-4034 (Bio-Rad Laboratories, Hercules, Calif.). The reaction mix was made with all components added to one 50 μL reaction and 20 μL was pipetted into two separate wells for droplet generation using the QX200 ddPCR system (Bio-Rad Laboratories, Hercules, Calif.). The droplet reactions from these wells were added each to a separate plate where one was thermal cycled using the standard thermal cycling protocol 95° C. for 5 minutes, 40 cycles of: 95° C. for 30 seconds and 50° C. for 1 minute, 4° C. for 5 minutes, 90° C. for 5 minutes, 4° C. hold and the other was thermal cycled using the split cycle thermal cycling protocol 95° C. for 5 minutes, 10 cycles of: 95° C. for 30 seconds and 40° C. for 1 minute, 30 cycles of: 95° C. for 30 seconds and 50° C. for 1 minute, 4° C. for 5 minutes, 90° C. for 5 minutes, 4° C. hold. The table shows that the copies per microliter concentrations were 25% higher in the split cycled well compared to the standard one temperature thermal cycling protocol. Further repeated experiments showed more efficient amplification was consistently seen as fewer mid-amplitude positives and quantification of 25-50% higher copies per microliter when the split cycle thermal cycling protocol was used in combination with assays having 5' tail regions (shown in FIG. 1).

| Thermalcycling Protocol | 40 cycles: 50° C. | 10 cycles: 40° C. 30 cycles: 50° C. |
|---|---|---|
| Copies/μL | 67.8 | 89.5 |

An alignment is provided below. The alignment of the human microRNA let 7 family sequences with the sequences that differ from the let-7a-5p highlighted in bold and underlined (SEQ ID NOs:4-12, respectively).

```
hsa-let-7a-5p
A A C T A T A C A A C C T A C T A C C T C A hsa-let-7b-5p
A A C C A C A C A A C C T A C T A C C T C A hsa-let-7c-5p
A A C C A T A C A A C C T A C T A C C T C A hsa-let-7d-5p
A A C T A T G C A A C C T A C T A C C T C T hsa-let-7e-5p
A A C T A T A C A A C C T C C T A C C T C A hsa-let-7f-5p
A A C T A T A C A A T C T A C T A C C T C A hsa-let-7g-5p
A A C T G T A C A A A C T A C T A C C T C A hsa-let-7i-5p
A A C A G C A C A A A C T A C T A C C T C A hsa-miR-98-5p
A A C A A T A C A A C T T A C T A C C T C A
```

Discrimination of each of these 9 highly similar microRNAs was achieved using a combination of the split cycle thermal cycling with the reverse transcription primer having the homopolymer region interspersed with a single, non-homopolymer nucleotide, the discriminating nucleotide placed within 1, 2, 3, or 4 of the 3' end of the primer(s), and in some cases an added mismatch to further destabilize binding of the primer to the incorrect target. The results of the assay as shown below:

| Assay\RNA Template Crossreactivity(%) | A | B | C | D | E | F | G | I | 98 |
|---|---|---|---|---|---|---|---|---|---|
| Let7A | 98.7 | 0.7 | 0.7 | 0.0 | 1.7 | 0.4 | 0.2 | 0.0 | N/A |
| Let7B | 0.1 | 100.0 | 0.1 | 0.1 | 0.1 | 0.0 | 0.1 | 0.1 | 1.6 |
| Let 7C | 0.1 | 3.5 | 100.0 | 0.0 | 0.1 | 0.1 | 0.0 | 0.0 | 0.8 |
| Let7D | 0.0 | 0.0 | 0.0 | 100.0 | 0.0 | 0.0 | 0.1 | 0.0 | 0.1 |
| Let7E | 0.0 | 0.0 | 0.0 | 0.0 | 95.6 | 0.0 | 0.0 | 0.0 | 0.0 |
| Let7F | 0.0 | 0.0 | 0.0 | 0.0 | 0.0 | 100.0 | 0.5 | 0.0 | N/A |
| Let7G | 0.1 | 0.0 | 0.0 | 0.0 | 0.0 | 0.1 | 100.0 | 0.1 | 0.9 |
| Let7I | 0.2 | 0.1 | 0.1 | 0.0 | 0.1 | 0.0 | 0.1 | 100.0 | 0.5 |
| miR98 | 0.0 | 0.0 | 0.0 | 0.0 | 0.0 | 0.1 | 0.0 | 0.0 | 100.0 |

The percent RNA amplified and detected for each of the family member microRNAs are shown above for each of the 9 different assays. The assay name is shown along the left vertical axis and the synthetic microRNA template added is shown along the top horizontal axis. The chart shows the percent of the sample that was amplified and measured.

Figure 3A:
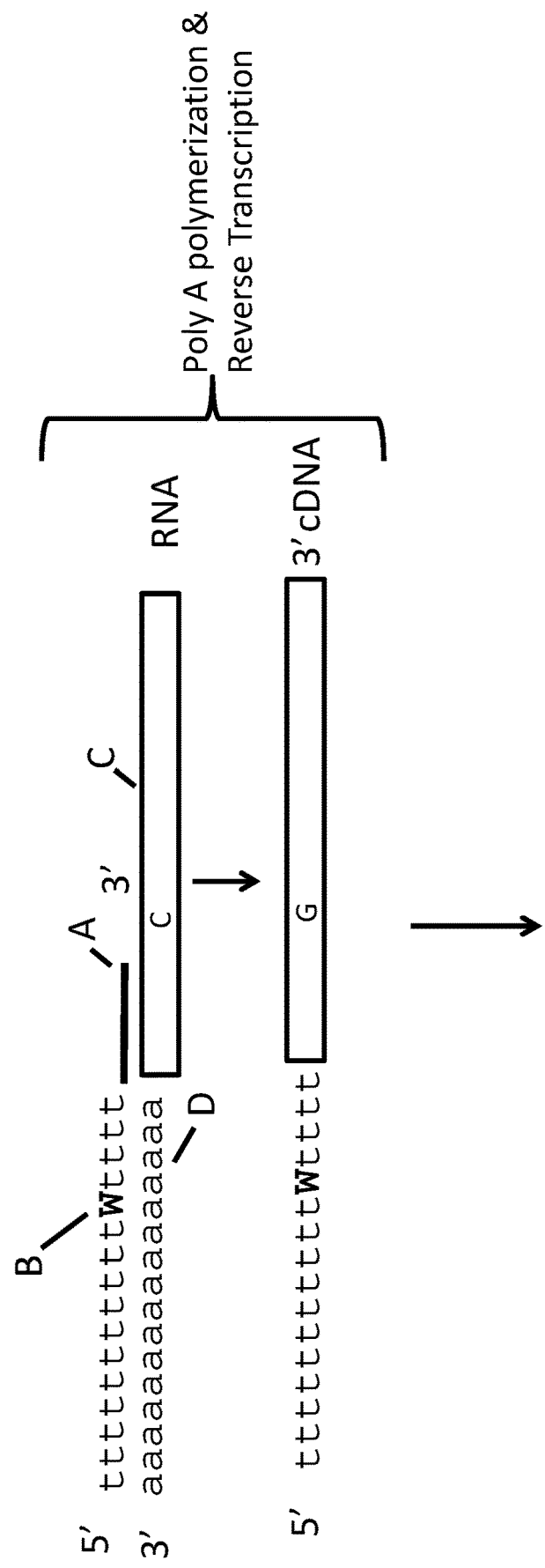
FIGS. 3A, 3B, and 3C schematically depict an embodiment of the method in which a polyA sequence is present on, or added to, an RNA molecule, which is subsequently reverse transcribed to generate the target DNA.
Figure 3B:
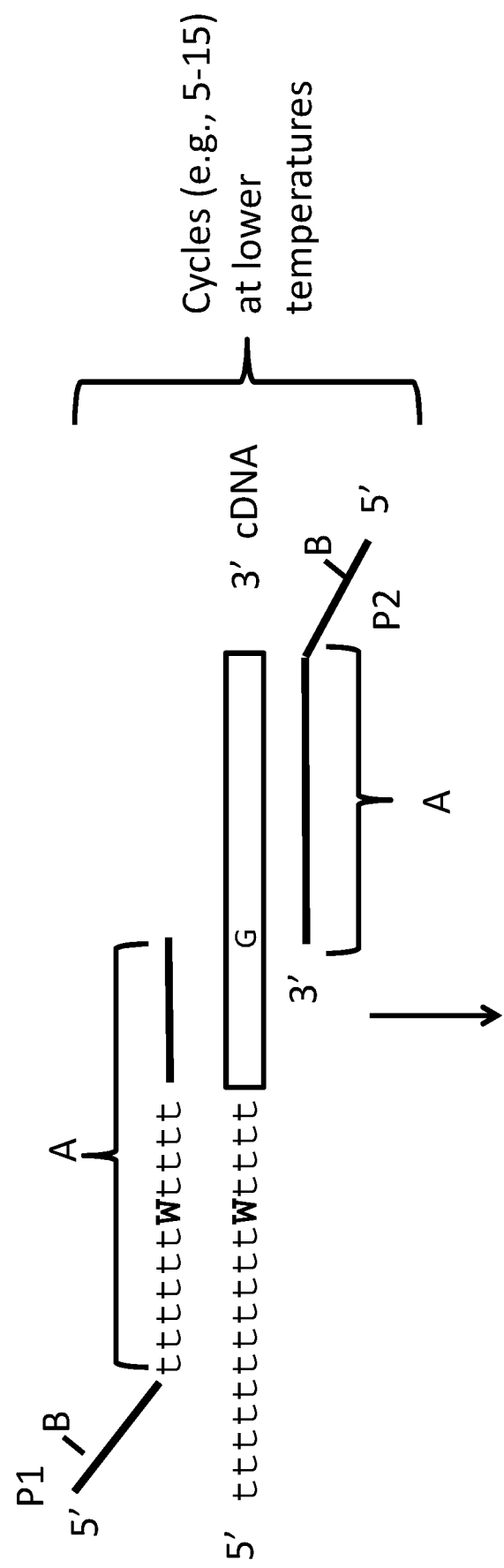
Figure 3C:
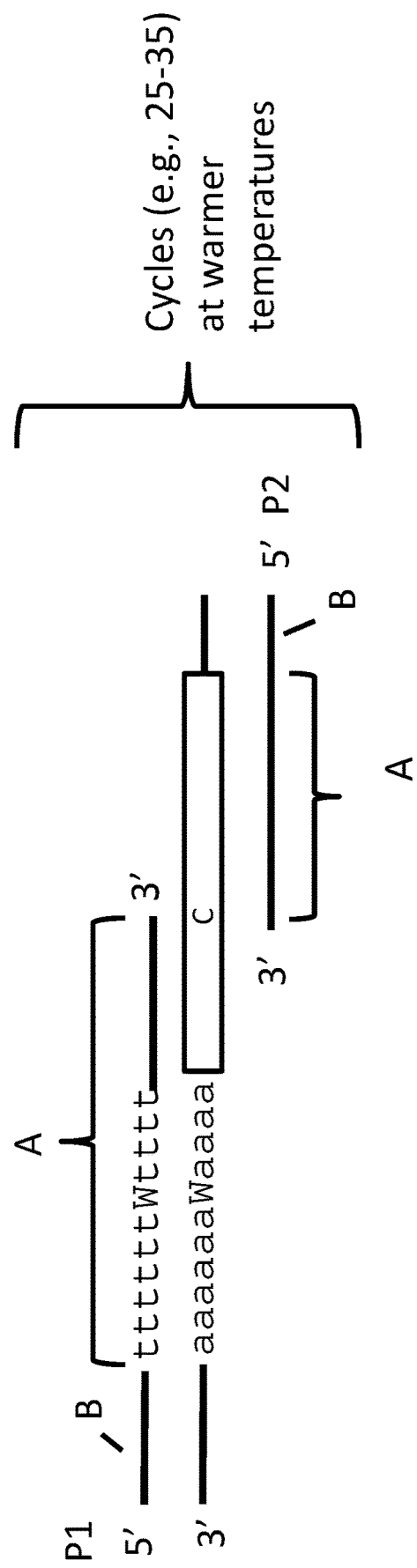
Figure 4B:
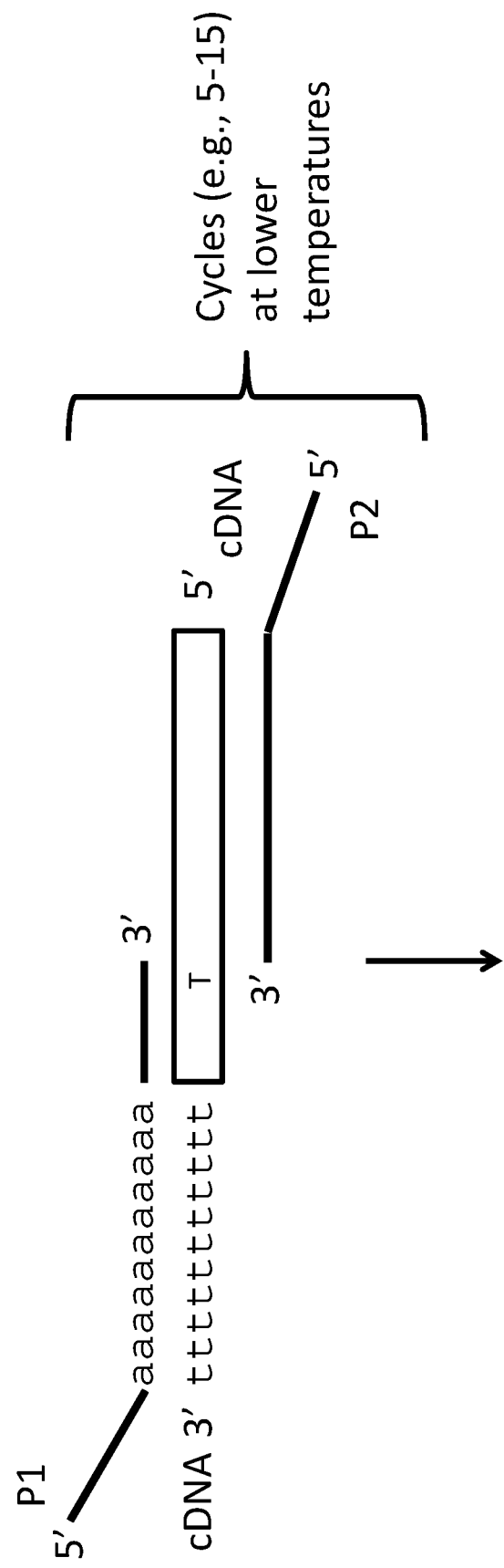
Figure 4C:
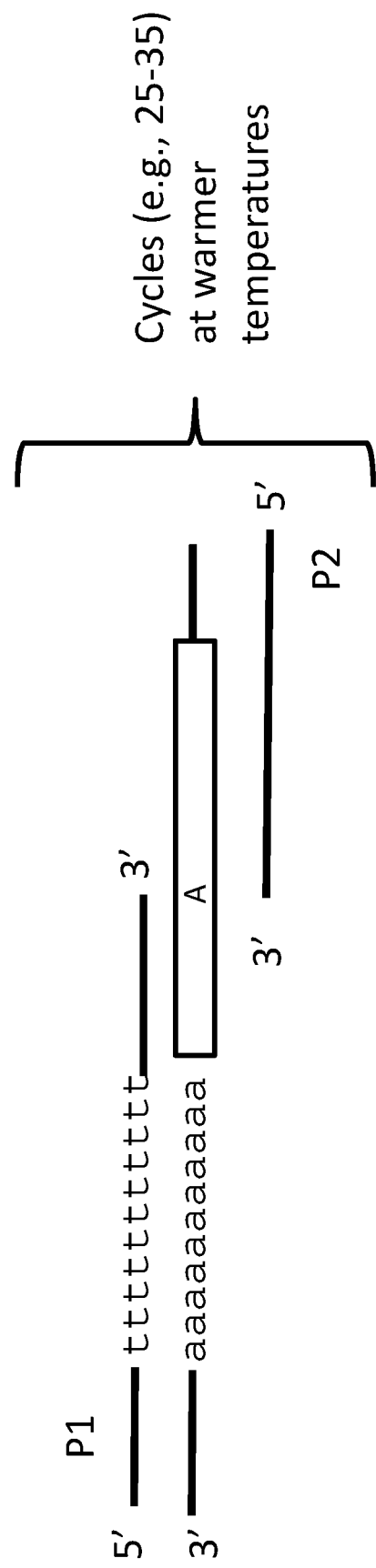
Figure 5A:
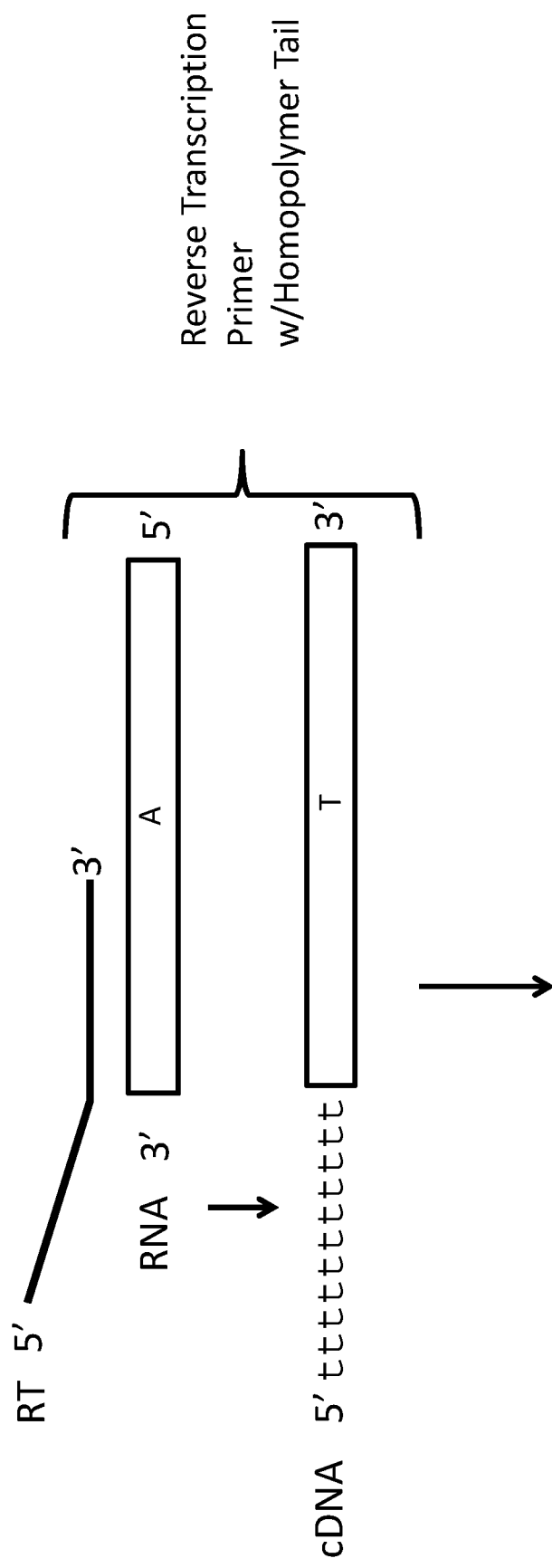
FIGS. 5A, 5B, and 5C schematically illustrate additional aspects in which a homopolymeric sequence (SEQ ID NO:18 (poly-T)) is added to the initial RNA 3' end by using a non-enzymatic reaction (e.g., by tailed reverse transcription primer). In the embodiment shown, polyT is added to the cDNA using a tailed reverse transcription primer in FIG. 5A, though other nucleotides and other homopolymers (e.g., polyA, polyU, polyG, polyC) can be added.
Figure 5B:
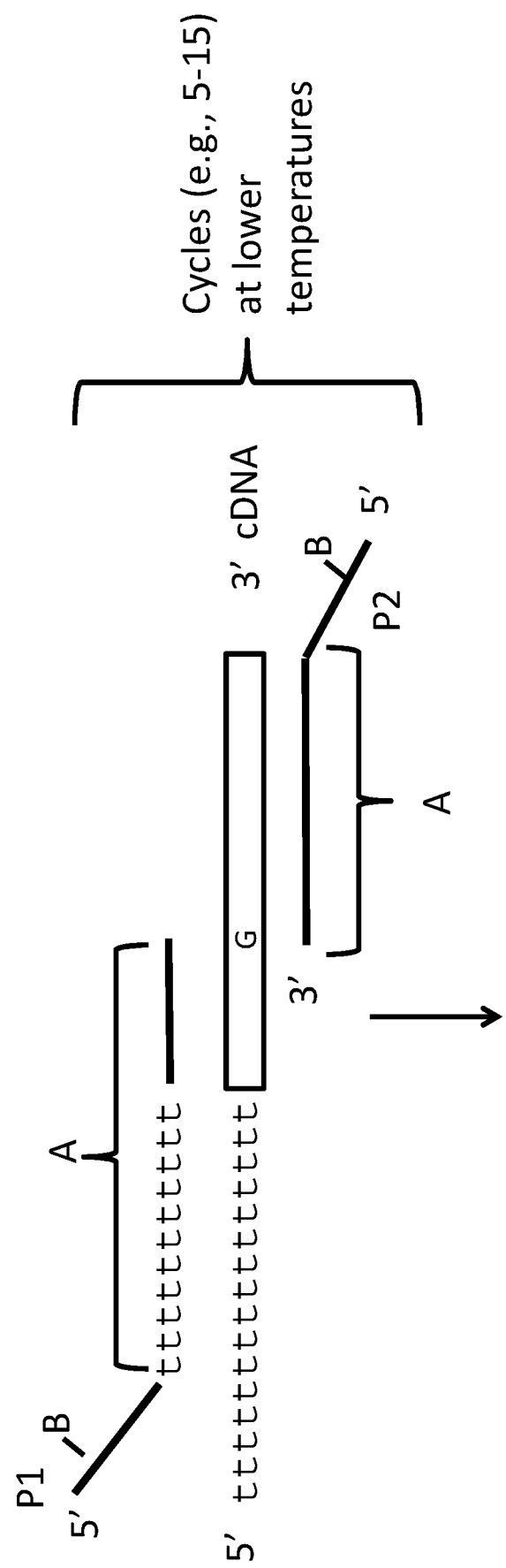
Figure 5C:
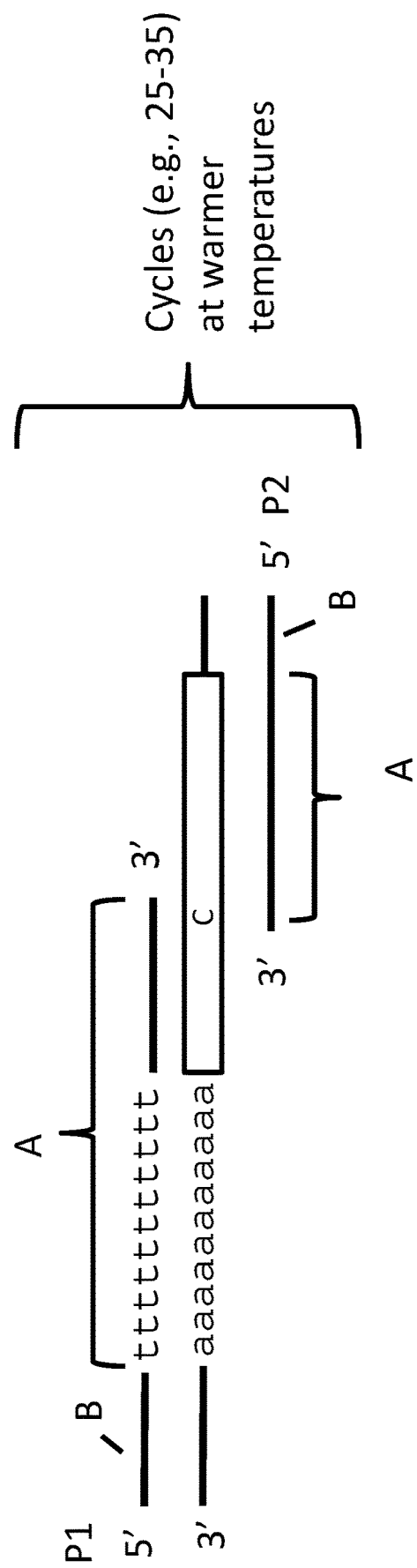

Synthetic microRNA for all 9 hsa-miR-let-7 (22 nucleotides each), the reverse transcription primer and 5' tailed assay primers were purchased (Integrated DNA Technologies, Coralville, Iowa). Synthetic microRNA had a homopolymer region of poly adenosine added to the microRNA using a poly adenylase enzyme (New England Biolabs, Ipswich, Mass.). This poly adenylated synthetic RNA was then added to a gene specific reverse transcription reaction using iScript Select cDNA synthesis kit cat #170-8896 (Bio-Rad Laboratories, Hercules, Calif.) and the reverse transcription primer with a homopolymer having partial complementarity to the poly adenylated region and synthetic microRNA as shown in FIG. 3A. The cDNA generated in the reverse transcription reaction was added directly to EvaGreen ddPCR Supermix Cat #186-4034 (Bio-Rad Laboratories, Hercules, Calif.) with the 5' tailed primers described in FIGS. 3 B & 3C. Cross reactivity or off-target amplification for the 9 nearly identical microRNA targets from the let-7 family shown in panel A was assessed by testing each discriminating assay individually with each of the 9 targets. Percent cross reactivity was calculated by setting the concentration of the target detected with a non-discriminating assay (FIG. 1) as 100%. Cross reactivity was calculated by dividing the concentration of the target that was amplified when each of the 9 targets were added individually to each assay by the concentration for 100% target amplification. All assays tested were able to discriminate with less than 4% cross reactivity for all 9 targets (less than 1% cross reactivity for with the exception of three 1.6, 1.7 and 3.5%) (B). Some microRNA methods need to sacrifice efficiency in order to obtain low cross reactivity but with the methods described here we demonstrate that we are able to obtain a high degree of specificity (low cross reactivity) with 100% efficiency.

All documents (for example, patents, patent applications, books, journal articles, or other publications) cited herein are incorporated by reference in their entirety and for all purposes, to the same extent as if each individual document was specifically and individually indicated to be incorporated by reference in its entirety for all purposes. To the extent such documents incorporated by reference contradict the disclosure contained in the specification, the specification is intended to supersede and/or take precedence over any contradictory material.

Many modifications and variations of this invention can be made without departing from its spirit and scope, as will be apparent to those skilled in the art. The specific embodiments described herein are offered by way of example only and are not meant to be limiting in any way.

What is claimed is:

1. A method of quantitating an amount of a target DNA template in a sample comprising:
   a) forming a plurality of mixture partitions, wherein the mixture partitions comprise:
      i) the target DNA template;
      ii) a thermostable DNA dependent DNA polymerase; and
      iii) a forward and a reverse amplification primer, wherein
      the amplification primers comprise a 3' hybridization region that hybridizes to the target DNA template and primes template directed extension of the primer in the presence of the DNA dependent DNA polymerase;
      the forward or the reverse amplification primer further comprises a 5' tail region that is not complementary to the target DNA template; and
   b) performing end-point amplification of the target DNA template in the mixture partitions by a polymerase chain reaction, wherein the thermal cycling conditions comprise a first set of temperature cycles and a second set of temperature cycles, wherein the second set of temperature cycles comprises an annealing temperature that is at least 5° C. higher than an annealing temperature of the first set of temperature cycles, and wherein one or more 3' hybridization regions have a melting temperature (Tm) below the second annealing temperature; and c) detecting the presence or absence of amplified target DNA template in the mixture partitions with an intercalating dye that produces a signal when intercalated in double stranded DNA and determining the fraction of partitions where the target DNA template is present; thereby quantifying the amount of target DNA template in the sample.

2. The method of claim 1, wherein the 5' tail region of the forward or the reverse amplification primers or both have at least 50% GC content.

3. The method of claim 1, wherein the first cycling condition comprises 5-15 cycles.

4. The method of claim 1, wherein the thermal cycling conditions further comprise a third set of temperature cycles comprising an annealing temperature that is at least 5° C. higher than the annealing temperature of the second set of temperature cycles.

5. The method of claim 3, wherein the first cycling condition comprises 5-15 cycles of:
 i) a denaturation step;
 ii) a combined primer annealing and extension step; and
 iii) optionally, a second annealing and extension step at a higher temperature than in the first primer annealing and extension step.

6. The method of claim 1, wherein the second cycling condition comprises 10-50 cycles.

7. The method of claim 6, wherein the second cycling condition comprises 10-50 cycles of:
 i) a combined primer annealing and extension step; and
 ii) a denaturation step.

8. The method of claim 1, wherein the first cycling condition comprises an annealing temperature of less than 50° C.

9. The method of claim 1, wherein the second cycling condition comprises an annealing temperature of at least 50° C.

10. The method of claim 1, wherein the amplification primers hybridize to opposite strands of the target DNA template and flank a region of the target DNA template between 1-30 nucleotides in length.

11. The method of claim 1, wherein the amplification primers hybridize to opposite strands of the target DNA template such that 3' ends of the primers hybridize to adjacent nucleotide positions in the target DNA template.

12. The method of claim 1, wherein the amplification primers hybridize to opposite strands of the target DNA template and the 3' ends of the amplification primers overlap when hybridized to the target DNA template.

13. The method of claim 1, wherein the 3' hybridization regions of the amplification primers are at least 8 or more nucleotides in length, and less than 30 nucleotides in length.

14. The method of claim 1, wherein the target DNA template is less than 30 nucleotides in length.

15. The method of claim 1, wherein the 5' tail region is at least 5 nucleotides in length.

16. The method of claim 1, wherein the 3' hybridization region of the forward or the reverse amplification primer comprises a discriminatory nucleotide, wherein the discriminatory nucleotide is complementary to the target DNA template but is not complementary to a second DNA template having a polymorphism in the region to which the amplification primer comprising the discriminatory nucleotide is hybridized, relative to the target DNA template, and wherein the discriminatory nucleotide is at the ultimate position from the 3' end of the primer or is 1, 2, 3, 4, or 5 nucleotides from the 3' end.

17. The method of claim 1, wherein the 3' hybridization region of the forward or reverse amplification primer comprises a homopolymeric region of at least 5 nucleotides, wherein the homopolymeric region comprises a polyadenine region or a polythymine region.

18. The method of claim 17, wherein the method comprises adding a homopolymeric region to the target DNA template by contacting the target DNA template with a terminal transferase enzyme.

19. The method of claim 1, wherein the forming of the plurality of mixture partitions comprising the target DNA template comprises reverse transcribing a target RNA template to form the target DNA template, and wherein the reverse transcribing the target RNA template comprises hybridizing a reverse transcription primer to the target RNA template, wherein the target RNA template is polyadenylated at the 3' end, and the reverse transcription primer comprises from 3' to 5':
 i) a 3' hybridization region that hybridizes to the target RNA template nucleic acid; and one of:
 ii) a homopolymeric region that is complementary to a region of the polyadenylated 3' end of the target RNA template; or
 iii) a region that is homopolymeric except has one or two nucleotides that are different from remaining nucleotides in the region, wherein the region, except for said one or two nucleotides, is complementary to a region of the polyadenylated 3' end of the target RNA template.

20. The method of claim 19, wherein the homopolymeric region comprises a polythymine region or a polyadenine region, wherein the homopolymeric region is at least 5 nucleotides in length.

21. The method of claim 19, wherein reverse transcribing the target RNA template comprises hybridizing a reverse transcription primer to the target RNA template and generating a cDNA, wherein the target RNA template is polyadenylated at the 3' end and the cDNA has a complementary polyT sequence at the 5' end of the cDNA, and the method further comprises adding a homopolymeric region to the 3' end of the cDNA, thereby generating a cDNA having homopolymeric sequences at 5' and 3' ends.

* * * * *

SEQUENCE LISTING

<160> NUMBER OF SEQ ID NOS: 35

<210> SEQ ID NO 1
<211> LENGTH: 61
<212> TYPE: DNA
<213> ORGANISM: Artificial Sequence
<220> FEATURE:
<223> OTHER INFORMATION: synthetic oligonucleotide primer
<220> FEATURE:
<221> NAME/KEY: misc_feature
<222> LOCATION: (1)..(10)
<223> OTHER INFORMATION: n is a, c, g or t; n may be present/absent
<220> FEATURE:
<221> NAME/KEY: misc_feature
<222> LOCATION: (12)..(30)
<223> OTHER INFORMATION: n is t; may be present or absent
<220> FEATURE:
<221> NAME/KEY: misc_feature
<222> LOCATION: (33)..(51)
<223> OTHER INFORMATION: n is t; may be present or absent
<220> FEATURE:
<221> NAME/KEY: misc_feature
<222> LOCATION: (52)..(61)
<223> OTHER INFORMATION: n is a, c, g or t; n may be present/absent
      (e.g., 1-5, 2-5, or 2-10)
<220> FEATURE:
<221> NAME/KEY: misc_feature
<222> LOCATION: (52)..(61)
<223> OTHER INFORMATION: sequence is complementary to a portion of a
      non-polyA region adjacent a the polyA tail

<400> SEQUENCE: 1
nnnnnnnnnn tnnnnnnnnn nnnnnnnnnn ytnnnnnnnn nnnnnnnnnn nnnnnnnnnn      60 n                                                                      61

<210> SEQ ID NO 2
<211> LENGTH: 15
<212> TYPE: DNA
<213> ORGANISM: Artificial Sequence
<220> FEATURE:
<223> OTHER INFORMATION: synthetic RT primer sequence

<400> SEQUENCE: 2
tttttctttt tacgc                                                       15

<210> SEQ ID NO 3
<211> LENGTH: 15
<212> TYPE: DNA
<213> ORGANISM: Artificial Sequence
<220> FEATURE:
<223> OTHER INFORMATION: synthetic PCR primer complement to RT primer

<400> SEQUENCE: 3
gcgtaaaaag aaaaa                                                       15

<210> SEQ ID NO 4
<211> LENGTH: 22
<212> TYPE: DNA
<213> ORGANISM: Artificial Sequence
<220> FEATURE:
<223> OTHER INFORMATION: synthetic hsa-let-7a-5p alignment sequence

<400> SEQUENCE: 4
aactatacaa cctactacct ca                                               22

<210> SEQ ID NO 5
<211> LENGTH: 22
<212> TYPE: DNA
<213> ORGANISM: Artificial Sequence

```
<220> FEATURE:
<223> OTHER INFORMATION: synthetic hsa-let-7b-5p alignment sequence

<400> SEQUENCE: 5
aaccacacaa cctactacct ca                                              22

<210> SEQ ID NO 6
<211> LENGTH: 22
<212> TYPE: DNA
<213> ORGANISM: Artificial Sequence
<220> FEATURE:
<223> OTHER INFORMATION: synthetic hsa-let-7c-5p alignment sequence

<400> SEQUENCE: 6
aaccatacaa cctactacct ca                                              22

<210> SEQ ID NO 7
<211> LENGTH: 22
<212> TYPE: DNA
<213> ORGANISM: Artificial Sequence
<220> FEATURE:
<223> OTHER INFORMATION: synthetic hsa-let-7d-5p alignment sequence

<400> SEQUENCE: 7
aactatgcaa cctactacct ct                                              22

<210> SEQ ID NO 8
<211> LENGTH: 22
<212> TYPE: DNA
<213> ORGANISM: Artificial Sequence
<220> FEATURE:
<223> OTHER INFORMATION: synthetic hsa-let-7e-5p alignment sequence

<400> SEQUENCE: 8
aactatacaa cctcctacct ca                                              22

<210> SEQ ID NO 9
<211> LENGTH: 22
<212> TYPE: DNA
<213> ORGANISM: Artificial Sequence
<220> FEATURE:
<223> OTHER INFORMATION: synthetic hsa-let-7f-5p alignment sequence

<400> SEQUENCE: 9
aactatacaa tctactacct ca                                              22

<210> SEQ ID NO 10
<211> LENGTH: 22
<212> TYPE: DNA
<213> ORGANISM: Artificial Sequence
<220> FEATURE:
<223> OTHER INFORMATION: synthetic hsa-let-7g-5p alignment sequence

<400> SEQUENCE: 10
aactgtacaa actactacct ca                                              22

<210> SEQ ID NO 11
<211> LENGTH: 22
<212> TYPE: DNA
<213> ORGANISM: Artificial Sequence
<220> FEATURE:
<223> OTHER INFORMATION: synthetic hsa-let-7i-5p alignment sequence

<400> SEQUENCE: 11
aacagcacaa actactacct ca                                              22
```

```
<210> SEQ ID NO 12
<211> LENGTH: 22
<212> TYPE: DNA
<213> ORGANISM: Artificial Sequence
<220> FEATURE:
<223> OTHER INFORMATION: synthetic hsa-miR-98-5p alignment sequence

<400> SEQUENCE: 12
aacaatacaa cttactacct ca                                              22

<210> SEQ ID NO 13
<211> LENGTH: 34
<212> TYPE: DNA
<213> ORGANISM: Artificial Sequence
<220> FEATURE:
<223> OTHER INFORMATION: synthetic target DNA sequence 5' to 3' -
      complement

<400> SEQUENCE: 13
tcccgctggc aactaacggt gacagacgtg ggct                                 34

<210> SEQ ID NO 14
<211> LENGTH: 34
<212> TYPE: DNA
<213> ORGANISM: Artificial Sequence
<220> FEATURE:
<223> OTHER INFORMATION: synthetic target sequence 5' to 3'

<400> SEQUENCE: 14
agcccacgtc tgtcaccgtt agttgccagc ggga                                 34

<210> SEQ ID NO 15
<211> LENGTH: 16
<212> TYPE: DNA
<213> ORGANISM: Artificial Sequence
<220> FEATURE:
<223> OTHER INFORMATION: synthetic poly-T sequence with
      non-homopolymeric nucleotide
<220> FEATURE:
<221> NAME/KEY: misc_feature
<222> LOCATION: (1)..(5)
<223> OTHER INFORMATION: n is a, c, g, or t

<400> SEQUENCE: 15
nnnnnttttt twtttt                                                     16

<210> SEQ ID NO 16
<211> LENGTH: 16
<212> TYPE: DNA
<213> ORGANISM: Artificial Sequence
<220> FEATURE:
<223> OTHER INFORMATION: synthetic poly-A sequence

<400> SEQUENCE: 16
aaaaaaaaaa aaaaaa                                                     16

<210> SEQ ID NO 17
<211> LENGTH: 11
<212> TYPE: DNA
<213> ORGANISM: Artificial Sequence
<220> FEATURE:
<223> OTHER INFORMATION: synthetic poly-A sequence with
      non-homopolymeric nucleotide

<400> SEQUENCE: 17
aaaawaaaaa a                                                          11
```

```
<210> SEQ ID NO 18
<211> LENGTH: 16
<212> TYPE: DNA
<213> ORGANISM: Artificial Sequence
<220> FEATURE:
<223> OTHER INFORMATION: synthetic poly-T sequence
<220> FEATURE:
<221> NAME/KEY: misc_feature
<222> LOCATION: (12)..(16)
<223> OTHER INFORMATION: n is t; may be wholly present (n = 5) or wholly
      absent (n = 0)

<400> SEQUENCE: 18
tttttttttt tnnnnn                                                       16

<210> SEQ ID NO 19
<211> LENGTH: 11
<212> TYPE: DNA
<213> ORGANISM: Artificial Sequence
<220> FEATURE:
<223> OTHER INFORMATION: synthetic poly-A sequence

<400> SEQUENCE: 19
aaaaaaaaaa a                                                            11

<210> SEQ ID NO 20
<211> LENGTH: 20
<212> TYPE: DNA
<213> ORGANISM: Artificial Sequence
<220> FEATURE:
<223> OTHER INFORMATION: synthetic sequence - Target RNA

<400> SEQUENCE: 20
ggtgcagaca gtggcaatca                                                   20

<210> SEQ ID NO 21
<211> LENGTH: 39
<212> TYPE: DNA
<213> ORGANISM: Artificial Sequence
<220> FEATURE:
<223> OTHER INFORMATION: synthetic sequence - Target RNA

<400> SEQUENCE: 21
ggctgcagac agtggcaatc aaaaaaaaaa aaaaaaaa                                39

<210> SEQ ID NO 22
<211> LENGTH: 19
<212> TYPE: DNA
<213> ORGANISM: Artificial Sequence
<220> FEATURE:
<223> OTHER INFORMATION: synthetic RT primer

<400> SEQUENCE: 22
tttttttttt gttttgat                                                     19

<210> SEQ ID NO 23
<211> LENGTH: 35
<212> TYPE: DNA
<213> ORGANISM: Artificial Sequence
<220> FEATURE:
<223> OTHER INFORMATION: synthetic cDNA sequence

<400> SEQUENCE: 23
tttttttttt gttttgatt gccactgtct gcacc                                   35

<210> SEQ ID NO 24
```

```
<211> LENGTH: 14
<212> TYPE: DNA
<213> ORGANISM: Artificial Sequence
<220> FEATURE:
<223> OTHER INFORMATION: synethetic PCR primer 1

<400> SEQUENCE: 24
tcgggtgcag acag                                                     14

<210> SEQ ID NO 25
<211> LENGTH: 17
<212> TYPE: DNA
<213> ORGANISM: Artificial Sequence
<220> FEATURE:
<223> OTHER INFORMATION: synthetic PCR primer 2

<400> SEQUENCE: 25
aggttgtttt tgattgc                                                  17

<210> SEQ ID NO 26
<211> LENGTH: 33
<212> TYPE: DNA
<213> ORGANISM: Artificial Sequence
<220> FEATURE:
<223> OTHER INFORMATION: synthetic PCR product

<400> SEQUENCE: 26
aggttgtttt tgattgccac tgtctgcacc cga                                33

<210> SEQ ID NO 27
<211> LENGTH: 33
<212> TYPE: DNA
<213> ORGANISM: Artificial Sequence
<220> FEATURE:
<223> OTHER INFORMATION: synthetic PCR product (reverse complement)

<400> SEQUENCE: 27
tcgggtgcag acagtggcaa tcaaaaacaa cct                                33

<210> SEQ ID NO 28
<211> LENGTH: 10
<212> TYPE: DNA
<213> ORGANISM: Artificial Sequence
<220> FEATURE:
<223> OTHER INFORMATION: synthetic RT primer

<400> SEQUENCE: 28
tgattgccac                                                          10

<210> SEQ ID NO 29
<211> LENGTH: 20
<212> TYPE: DNA
<213> ORGANISM: Artificial Sequence
<220> FEATURE:
<223> OTHER INFORMATION: synthetic cDNA sequence

<400> SEQUENCE: 29
tgattgccac tgtctgcacc                                               20

<210> SEQ ID NO 30
<211> LENGTH: 21
<212> TYPE: DNA
<213> ORGANISM: Artificial Sequence
<220> FEATURE:
<223> OTHER INFORMATION: synthetic oligonucleotide sequence

<400> SEQUENCE: 30
```

```
tgattgccac tgtctgcagt a                                              21

<210> SEQ ID NO 31
<211> LENGTH: 38
<212> TYPE: DNA
<213> ORGANISM: Artificial Sequence
<220> FEATURE:
<223> OTHER INFORMATION: synthetic terminal transferase sequence

<400> SEQUENCE: 31
tttttttttt tttttttttg attgccactg tctgcacc                            38

<210> SEQ ID NO 32
<211> LENGTH: 30
<212> TYPE: DNA
<213> ORGANISM: Artificial Sequence
<220> FEATURE:
<223> OTHER INFORMATION: synthetic RT primer

<400> SEQUENCE: 32
tttttttttt ttttgtttt tgattgccac                                      30

<210> SEQ ID NO 33
<211> LENGTH: 21
<212> TYPE: DNA
<213> ORGANISM: Artificial Sequence
<220> FEATURE:
<223> OTHER INFORMATION: synthetic PCR primer 2

<400> SEQUENCE: 33
aggttttttt tttttgattg c                                              21

<210> SEQ ID NO 34
<211> LENGTH: 36
<212> TYPE: DNA
<213> ORGANISM: Artificial Sequence
<220> FEATURE:
<223> OTHER INFORMATION: synthetic PCR product

<400> SEQUENCE: 34
aggttttttt ttttgattgc cactgtctgc acccga                              36

<210> SEQ ID NO 35
<211> LENGTH: 36
<212> TYPE: DNA
<213> ORGANISM: Artificial Sequence
<220> FEATURE:
<223> OTHER INFORMATION: synthetic PCR product (reverse complement)

<400> SEQUENCE: 35
tcgggtgcag acagtggcaa tcaaaaaaaa aaacct                              36
```